US006343257B1

(12) United States Patent
Olender et al.

(10) Patent No.: US 6,343,257 B1
(45) Date of Patent: Jan. 29, 2002

(54) IDENTIFYING PHARMACOPHORE CONTAINING COMBINATIONS OF SCAFFOLD MOLECULES AND SUBSTITUENTS FROM A VIRTUAL LIBRARY

(75) Inventors: Roberto Olender, Rehovot; Rakefet Rosenfeld, Macabim, both of (IL)

(73) Assignee: Peptor Ltd., Rehovot (IL)

( * ) Notice: Subject to any disclaimer, the term of this patent is extended or adjusted under 35 U.S.C. 154(b) by 0 days.

(21) Appl. No.: 09/296,747

(22) Filed: Apr. 23, 1999

(51) Int. Cl.$^7$ .................. G01N 33/48; G01N 33/50; G01N 31/00; G06F 19/00; G06F 17/00
(52) U.S. Cl. .................. 702/19; 702/27; 706/45; 706/47
(58) Field of Search .................. 702/27; 364/496; 395/606

(56) References Cited

U.S. PATENT DOCUMENTS 6,188,965 B1 * 2/2001 Mayo et al. .................. 702/27

FOREIGN PATENT DOCUMENTS

| WO | 95/33765 | 8/1995 |
| WO | 98/47089 | 10/1998 |

OTHER PUBLICATIONS

Bures M.G. et al., "New Molecular Modeling Tools Using Three–Dimensional Chemical Substructures", J. Chem. Inf. Comput. Sci. vol. 34, pp. 218–223 (1994).*
Martin, Y., "3D Database Searching in Drug Design", *J. Medicinal Chemistry*, 35(12): 2145–2154, 1992.

Dahiyat et al, "De Novo Protein Design: Fully Automated Sequence Selection", *Science*, 278: 82–87, 1997.
Good et al, "Three–Dimensional Structure Database Searches", *Reviews in Computational Chemistry*, 7: 67–117, 1996.

* cited by examiner

*Primary Examiner*—Kenneth R. Horlick
*Assistant Examiner*—Teresa Strzelecka
(74) *Attorney, Agent, or Firm*—D'vorah Graeser

(57) ABSTRACT

A method for constructing a potentially pharmaceutically useful molecule that displays a predefined pharmacophore associated with a desired biological activity is disclosed. The pharmacophore is first used to screen a virtual library of scaffolds, described by three-dimensional coordinates, in order to identify one or more scaffold(s) which could potentially display substituents that alone or together with scaffold atoms comprise a pharmacophore. The screening process involves first placing rotamers from a virtual library of substituents onto each attachment point of each scaffold, and then examining the resultant Virtual Combinatorial Library (VCL) according to one or more parameters required by the pharmacophore. Preferably, the VCLs are filtered with a series of filters of increasing complexity, in order to eliminate those scaffolds incompatible with the pharmacophore of choice and to identify scaffolds which could display substituents compatible with the pharmacophore, as well the corresponding substituent rotamers themselves. The compatible scaffolds and corresponding substituents are combined to represent one or more molecule or molecules containing the desired pharmacophore. Thus, the method of the present invention is able to efficiently screen very large numbers of molecular entities for the presence of a desired pharmacophore.

22 Claims, 4 Drawing Sheets

| | |
|---|---|
| STEP 1 | PROVIDE A PHARMACOPHORE AND 2 VIRTUAL LIBRARIES |
| STEP 2 | DETERMINE A MATRIX OF ALL DISTANCES BETWEEN PAIRS OF DESCRIPTORS IN PHARMACOPHORE |
| STEP 3 | SELECT A BACKBONE SCAFFOLD |
| STEP 4 | CONSTRUCT THE CORRESPONDING SUPER-STRUCTURE OF THE VCL BY CONNECTING ALL SUBSTITUENTS TO EACH SCAFFOLD ATTACHMENT POINT |
| STEP 5 | ASSIGN DESCRIPTOR TYPES TO ALL RELEVANT ATOMS |
| STEP 6 | ELIMINATE ROTAMERS WHICH CLASH WITH BACKBONE |
| STEP 7 | MARK PAIRS OF ROTAMERS WHICH CLASH BETWEEN THEMSELVES |
| STEP 8 | ELIMINATE INCOMPATIBLE BACKBONE DESCRIPTOR TYPE ASSIGNMENTS |
| STEP 9 | FILTER OUT SCAFFOLDS INCOMPATIBLE WITH THE ON-SCAFFOLD SUB- PHARMACOPHORE (RETURN TO STEP 3 IF SCAFFOLD IS REJECTED) |
| STEP 10 | CONSTRUCT MATRIX OF ALL PAIRWISE INTERACTIONS BETWEEN ALL REMAINING ROTAMERS |
| STEP 11 | FILTER ACCORDING TO DESCRIPTOR TYPE |
| STEP 12 | FILTER ACCORDING TO DESCRIPTOR IDENTITY |
| STEP 13 | FILTER OUT ON-SCAFFOLD DESCRIPTOR ASSIGNMENT THAT ARE INCOMPATIBLE WITH FULL PHARMACOPHORE AND REPEAT STEP 9 |
| STEP 14 | REPEAT STEPS 12 AND 13 |
| STEP 15 | FILTER ACCORDING TO TRIPLETS OF ROTAMERS |
| STEP 16 | REPEAT STEPS 12 AND 14 |
| STEP 17 | FORM PHYSICALLY REALIZABLE MOLECULES FROM REMAINING COMBINATION(S) OF SCAFFOLD AND ROTAMERS AND CHECK FOR EXISTENCE OF PHARMACOPHORE |
| STEP 18 | RETURN TO STEP 3 |

FIG.2

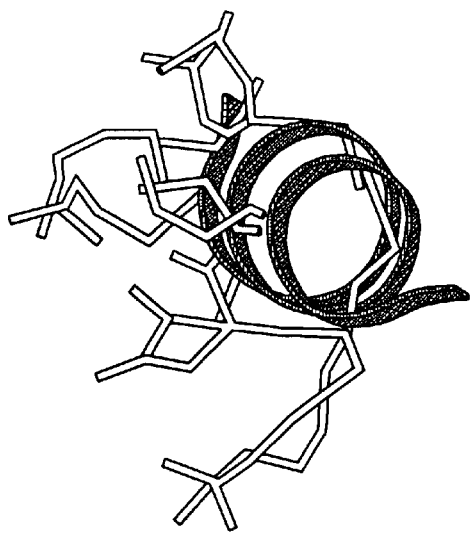
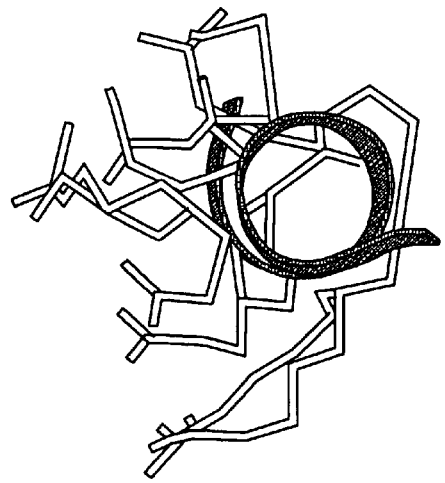
FIG.4A  FIG.4B
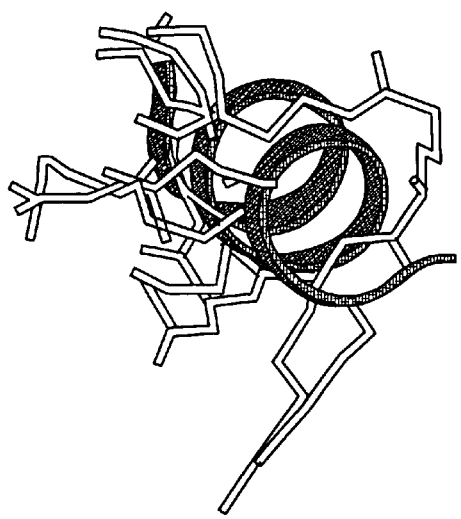
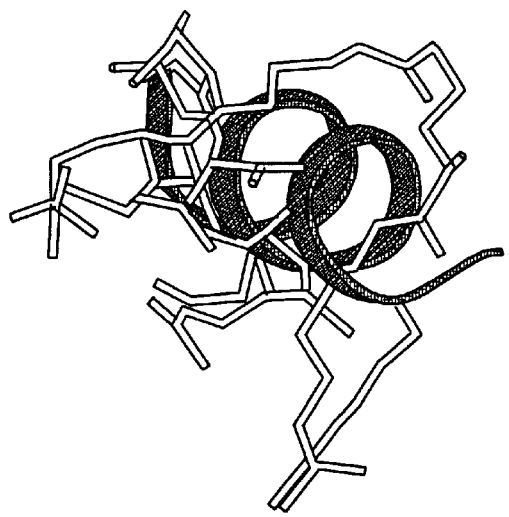
FIG.4C  FIG.4D

IDENTIFYING PHARMACOPHORE CONTAINING COMBINATIONS OF SCAFFOLD MOLECULES AND SUBSTITUENTS FROM A VIRTUAL LIBRARY

FIELD OF THE INVENTION

The present invention relates to a method for constructing virtual libraries of molecules and screening these libraries for the existence of a predefined structural motif, and in particular identifying molecules which meet the constraints imposed by a pharmacophore.

BACKGROUND OF THE INVENTION

A classical approach to the problem of drug-lead optimization—the so-called "lead explosion" method—involves making large numbers of slightly modified analogs of the drug lead compound. Yet while in some cases this can result in analogs with largely increased binding affinities to the desired target, the major drawback of this method is that it results in a set of highly similar molecules. Thus, if the original lead compound fails at a later stage of the drug development process, for reasons which are not directly related to its target binding capabilities, such as problems of solubility, toxicity, or bioavailability for example, there is a good chance that the majority of the second generation analogs will fail likewise.

A more recent approach that overcomes this drawback involves identifying from a set of lead compounds an "active structural motif"—in particular but not limited to a pharmacophore—and searching, by computer algorithms, a database of compounds for its existence. The result of this search may be a set of diverse molecules that display the predefined structural motif [Y. C. Martin, 3D Database Searching in Drug Design, *J. Med. Chem.* 35, 2145(1992); A. C. Good and J. S. Mason, Three Dimensional Structure Database Searches, *Reviews in Comp. Chem.* 7, 67(1996)].

The pharmacophore has proven to be a highly valuable and useful concept in drug discovery and drug-lead optimization. A pharmacophore is defined as a distinct three dimensional (3D) arrangement of chemical groups essential for biological activity. Since a pharmaceutically active molecule must interact with one or more molecular structures within the body of the subject in order to be effective, and the desired functional properties of the molecule are derived from these interactions, each active compound must contain a distinct arrangement of chemical groups which enable this interaction to occur. The chemical groups, commonly termed descriptor centers, can be represented by (a) an atom or group of atoms; (b) pseudo-atoms, for example a center of a ring, or the center of mass of a molecule; (c) vectors, for example atomic pairs, electron lone pair directions, or the normal to a plane. Clearly, the ability to design, or identify from large databases, pharmaceutically useful molecules according to the pharmacophore would be highly effective both in the process of drug discovery and in the process of drug lead optimization.

The pharmacophore can be constructed either directly or indirectly. In the direct method and pharmacophore descriptor centers are inferred from studying the X-ray or NMR structure of a receptor-ligand complex, or by a shape-complementarity function analysis of the receptor binding site. In the indirect method the structure of the receptor is unknown and therefore the pharmacophore descriptor centers are inferred by overlaying the 3-dimensional conformations of active compounds and finding the common, overlapping functional groups.

The virtually screened databases may be commercially and/or publicly available or corporate databases of existing compounds, or virtual, existing solely on the computer. In both cases the size of the lists is commonly on the order of tens to hundreds of thousands of molecules. This size limitation, in particular for the virtual databases, commonly stems from limitations of disk space needed to store the library and the speed of the algorithms that are available to scan it.

Yet databases in the above size range comprise only a small subset of chemical space. For example, a database of 100 peptidomimetic scaffolds with 6 side-chain attachment points for the 18 (non-glycine or proline) natural amino acid sidechains can potentially combine to give $3 \times 10^9$ different molecules, well beyond the size that currently can be screened on available computers, in a reasonable amount of time. Furthermore, most pharmaceutically interesting molecules are flexible, adding an additional level of complexity to the problem. There exist methods that attempt to deal with flexible molecules by constrained optimization, yet these are computationally expensive—the optimization is a computationally demanding overhead on the database search itself. For example using the method of "template-forcing", in which an attempt is made to force each analog to fit the desired conformation, databases that can be virtually screened within a reasonable amount of time are on the orders of magnitude of $10^5$ different compounds. The optional approach is to represent each flexible molecule as a set of discrete conformations. Thus in the above example if the 18 sidechains are represented by a rotamer library of 10 conformations for each, the result will be a database of $3 \times 10^{15}$ entities, representing all possible discrete conformations of the $3 \times 10^9$ different molecules. Since with currently available tools it is not feasible to virtually scan even the smaller library of $3 \times 10^9$ molecules, a tool that enables the construction and screening of libraries of this size range within reasonable time is of high practical value.

The necessity to scan extraordinarily large number of entities in a search space also arises in the field of protein sequence design. In protein sequence design a large number of sequence combinations needs to be evaluated in searching for the one that optimally lends itself to a particular structure. One method that has been applied to this problem, the Dead-End Elimination algorithm, is related to the art of the present invention in that it utilizes a library of discrete conformations for each of the amino-acid side chains, and defines mathematical criteria for eliminating the vast majority of combinatorial possibilities without actually considering them formally. This algorithm has been successfully applied to the problem of protein design [B. I. Dahiyat and S. L. Mayo, De Novo Protein Design: Fully Automated Sequence Selection. *Science* 278,82(1997); PCT application No. WO 98/47089].

Thus, there is a widely recognized need for, and it would be highly advantageous to have, a method for constructing very large virtual databases of molecules which are potentially pharmaceutically useful, and for screening these molecules for the existence of a pharmacophore, representing the desired interactions of the useful molecule with one or more structures in the body of the subject.

SUMMARY OF THE INVENTION

The present invention features a method for constructing a potentially pharmaceutically useful molecule that contains a desired pharmacophore, associated with a specific biological activity.

One aspect of the present invention is a method for constructing a virtual combinatorial library (VCL), which is a set of abstract super-structures, none of which is a physically realizable entity. Each super-structure features a single chemical scaffold holding all possible substituents at all possible substituent attachment points, concurrently. This VCL represents a set of physically realizable discrete conformations of a defined set of molecular entities. This set may be very large, representing more than $10^{20}$ different 3-dimensional structures by a small number of such super-structures.

Another aspect of the present invention is a method for virtually screening this library for the existence of molecules that display a desired, predefined molecular structure, and in particular a pharmacophore.

The VCL is constructed from a virtual library of scaffolds, for example constrained peptidomimetic backbones, and a virtual library of substituents that can be placed at each of a set of predefined attachment positions on each scaffold. The VCL is constructed by placing all rotamers from the virtual library of substituents onto each of the attachment points on each scaffold, concurrently.

The scaffold library is a set of molecules described by three-dimensional coordinates, with a predefined set of attachment points onto which substituents may be chemically attached. The library of substituents is described by all physically realizable conformations of each of the chemical entities that can be chemically connected to the scaffold at said attachment points.

The active structural motif designated herein as the pharmacophore is used to screen the VCL of super-structures in order to identify the combinations of scaffolds and substituents which meet the constraints imposed by the pharmacophore.

The screening process involves the application of a series of filters of increasing complexity, in order to eliminate the substituents that are incompatible with the pharmacophore. Following the filtration process the method produces, from all combinations of scaffolds and substituents that remain, a molecule or molecules which display the desired pharmacophore.

The scaffolds can be any molecule containing at least one attachment point, and that can be represented by a set of discrete conformations. As a non-limiting example, constrained peptide backbones can be used as scaffolds, and amino acid side chains can be represented by rotamer libraries, which include all energetically favorable conformations of each amino acid.

The screening of the VCL is performed by iterative applications of a series of filters of increasing complexity, which efficiently identify and eliminate scaffolds and substituent rotamers that are incompatible with the desired pharmacophore, thereby eventually identifying those scaffolds and substituent rotamers which display the chemical and geometric requirements of the desired pharmacophore. These requirements are defined by a series of pharmacophore parameters. An illustrative example of such parameters may be, but is not limited to a matrix of all pair-wise distances between all pharmacophore descriptors. Thus, by the discretization of the conformational space of both scaffolds and substituents, and by the application of the sophisticated series of filters, the method of the present invention is able to scan very large virtual libraries, representing more than $10^{20}$ 3-dimensional structures, within reasonable computer time.

According to the present invention there is provided a method for identifying at least one molecule having the constraints imposed by a pharmacophore, each of these constraints being defined by at least one pharmacophore parameter, the steps of the method being performed by a data processor, the method comprising the steps of:

(a) providing a first virtual library of at least one scaffold, each scaffold containing at leas one attachment point for a substituent, and a set of three-dimensional coordinates for each atom of said scaffold;

(b) providing a second virtual library of a plurality of substituents, each of said plurality of substituents being described by a set of physically realizable discrete conformations, wherein each conformation of each of said plurality of substituents is a rotamer;

(c) concurrently adding all rotamers from said second virtual library to each attachment point of each scaffold to form the super-structures;

(d) assigning pharmacophore descriptors to all possible atoms or groups of atoms on the rotamers and on the scaffolds;

(e) applying a series of filters to each super-structure to test the compatibility of each rotamer in the super-structure to a pharmacophore parameter;

(f) eliminating any rotamer if said specific rotamer cannot exist in at least one combination that is compatible with all pharmacophore parameters;

(g) constructing molecules from combinations of remaining rotamers and scaffolds, and selecting those combinations that display the pharmacophore.

The method of the present invention can be described as a plurality of instructions being performed by a data processor, such that the method of the present invention can be implemented in hardware, software, firmware or a combination thereof. As software, the present invention can be implemented in any suitable programming language that is compatible with the computer hardware and operating system which is performing the instructions, and could easily be selected by one of ordinary skill in the art. Examples of such suitable programming languages include, but are not limited to, Fortran, C and C++.

BREF DESCRIPTION OF THE DRAWINGS

The invention is herein described, by way of example only, with reference to the accompanying drawings, wherein:

FIG. 2 shows a flow chart of an exemplary method for identifying a candidate molecule through a pharmacophore according to the present invention;

FIG. 4 shows 4 possible molecular entities that can mimic the structural motif of the receptor-binding helix of Growth Hormone, superimposed on this motif.

DESCRIPTION OF THE PREFERRED EMBODIMENTS

Figure 1A:
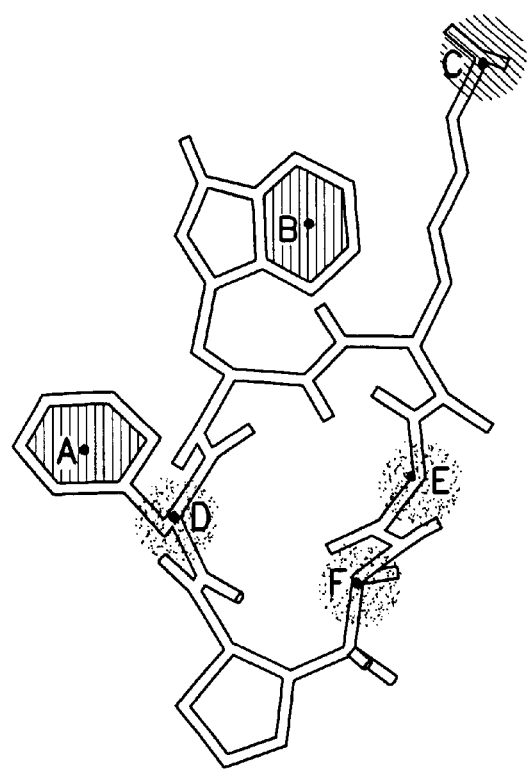
FIG. 1 shows two exemplary model pharmacophores derived from somatostatin, suitable for use with the method of the present invention.

The present invention provides a method for constructing potentially pharmaceutically useful molecules which contain a desired pharmacophore, associated with a specific biological activity. The pharmacophore is used to screen a Virtual Combinatorial Library (VCL), which is constructed from a virtual library of scaffolds and a virtual library of all energetically favorable conformations of a set of substituents, and identifying those scaffolds and substituents that can display the pharmacophore. The screening process involves first constructing the super-structures for each scaffold, and then examining each retainer in the resultant super-structure according to parameters defined by the pharmacophore. Preferably, the super-structures are filtered with a series of filters of increasing complexity, in order to identify rotamers that are incompatible with the pharmacophore and eliminate these from the VCL. The computational efficiency is attained by applying the filters in an order of increasing complexity, namely by initially applying filters that examine only pairs of rotamers, followed by filters that examine triplets, and then filters that examine higher order combinations if necessary. Following the application of all filters, a super-structure that is left, i.e. the combined scaffold and attached substituents, represents a set of physically realizable molecules that contain the desired pharmacophore. Thus, the method of the present invention is able to efficiently eliminate rotamers that are incompatible with the pharmacophore thereby allowing the screening of an enormous number of possible molecules without actually generating all of them.

In contrast to methods that screen large existing databases, the methods of the present invention construct virtual libraries of super-structures and virtually screen these libraries, and therefore have striking advantages over the known methods that screen 3D databases. These advantages include the following. First, the present invention can represent and screen very large sets of molecules, which may be orders of magnitude larger than existing databases screenable in a reasonable amount of time. Next, the present invention can construct virtual libraries with a selected set of substituents out of all possibilities, these substituents being selected such that they can present any of the desired chemical groups required by the pharmacophore. This aspect decreases the size of the VCL therefore making it more efficient to search. Also, the program can be easily distributed to run on a set of distinct computers or on a distributed memory parallel computer. This can be accomplished by splitting the scaffold library between the different processors.

The principles and operation of a method according to the present invention may be better understood with reference to the drawings and the accompanying description.

Referring now to the drawings, FIG. 1 shows illustrative pharmacophores, while FIG. 2 is a flowchart of an exemplary method for identifying a candidate molecule through a pharmacophore according to the present invention. The method requires two virtual libraries. These two virtual libraries are potentially useful for developing many different types of pharmaceutically useful molecules according to many different pharmacophores. As described in greater detail below, the method of the present invention must also receive the pharmacophore, against which the candidate molecules are compared in a process of filtration to eliminate those candidate molecules which cannot fulfill the restrictions imposed by the pharmacophore.

The first virtual library required by the method of the present invention is a library of scaffolds, which may be peptidic or non-peptidic, and which in the example of FIG. 1 is peptidic. For the purposes of clarity only and without intending to be limiting, the method of the present invention is described below with regard to a library of constrained peptide or peptidomimetic backbone scaffolds. Each scaffold is represented as a set of three-dimensional coordinates for each atom, as well as a list of atoms onto which various substituents may be attached. These atoms on a peptidic backbone may be the $C\alpha$ atoms of alpha and amino acids, or the nitrogens for a library of $N\alpha$-alkylated amino acids. In the present example these atoms are the $C\alpha$ atoms of the peptidic backbones, and are hereinafter referred to as "attachment points".

It will be recognized by the artisan that the methods of the present invention are applicable to non-peptide scaffolds as well, and that peptides are used herein as non-limiting illustrative examples of the operation of the method of the present invention.

By way of example, the method of the present invention is suitable for use with any constrained peptidic or peptidomimetic scaffolds, including those designated backbone cyclic peptide analogs containing N-alkylated amino acid analogs which are described in PCT application No. WO 95/33765, which is incorporated herein by reference in its entirety.

The second virtual library is a library of substituents which can be connected to the backbone scaffold at the attachment points. These substituents can be side chains of naturally occurring and/or non-naturally occurring amino acids, for example. Each such substituent may be described by a set of conformations, such that the library is a rotamer library.

The method must also receive the desired pharmacophore against which the candidate molecules are compared in the process of filtration. The pharmacophore is described as a set of atoms, chemical groups, pseudo-atoms or vectors, and the relative positions in space of each of these pharmacophore descriptors. Each descriptor, alone or in combination with its relative position, forms a pharmacophore parameter. Each pharmacophore descriptor can be an entity from the scaffold, an entity from the substituents or an entity from either the backbone scaffold or the substituents. An example of an entity from the scaffold is a $C\alpha$ atom of a peptidic backbone. An example of an entity from the substituents is a methyl group from an amino acid side chain. An example of an entity contributed by either the scaffold or the substituents is a hydrogen bond donor. Thus, the pharmacophore includes the pharmacophore descriptors, and the relative position of each descriptor with regard to all other descriptors comprising the pharmacophore.

Figure 1B:
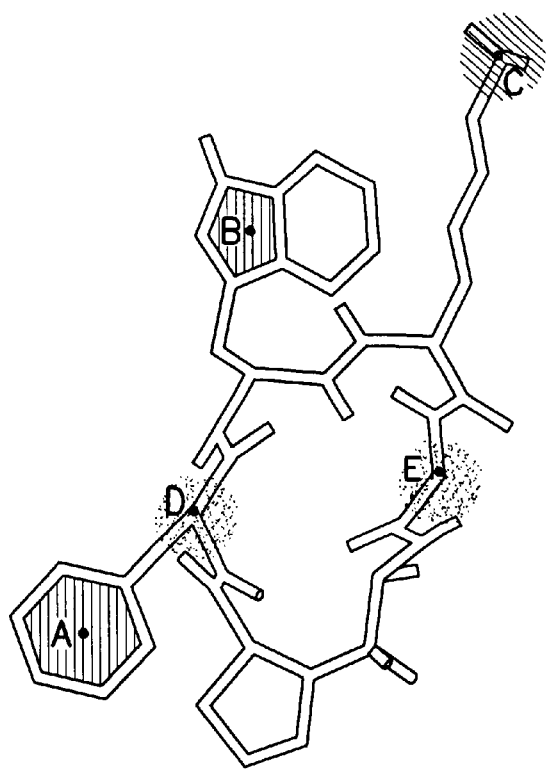

Two model somatostatin pharmacophores are depicted in FIGS. 1A and 1B, as displayed on a known analog of the hormone somatostatin, for the purposes of illustration only and without any intention of being limiting. The model pharmacophores were previously obtained from a set of known somatostatin analogs, and were used to test the method of the present invention as described in greater detail below in Example 1. The first model pharmacophore (FIG. 1A) features six pharmacophore descriptors, labeled as "A" through "F", presented on a cyclic peptide scaffold. Pharmacophore descriptors "A" through "C" are contributed by the sidechains of the substituents, while pharmacophore descriptors "D" through "F" are contributed by the backbone scaffold. The set of these pharmacophore descriptors "A" through "F" in combination with the relative position of each pharmacophore in space forms the pharmacophore.

For this purposes of illustration, each pharmacophore descriptor is shown as a filled circle, representing a descriptor center, with a pattern representing a descriptor type. As shown, vertical lines are used to indicate the center of the aromatic rings, slanted lines represent the nitrogen atom of $NH_3+$, and dots represent the $C\alpha$ atoms in the peptide backbone. Some descriptor types are shared, such that both pharmacophore descriptor "A" and pharmacophore descriptor "B" are centers of aromatic rings, as shown by the vertical lines.

Reference is now made to FIG. 2, which is a flowchart of an exemplary method according to the present invention for the purposes of description only and without intending to be limiting.

As shown in step 1 of FIG. 2, the method of the present invention begins with the provision of the desired pharmacophore, and of the two virtual libraries which were previously described. In step 2, the desired pharmacophore is translated into a matrix of all distances between all possible pairs of descriptors. This translation enables the pharmacophore to be considered as a set of pair wise interactions between all of the different pairs.

In step 3, a backbone scaffold is selected from the virtual library of backbone scaffolds. In step 4, the substituents from the virtual library of substituents are added to each of the backbone attachment points, in this case the Cα atoms of the peptidic backbone. If the backbone attachment points are Cα atoms, only Cα atoms from non-proline or glycine residues are used. For the purposes of illustration only and without intending to be limiting, for the present example the virtual library of substituents is a rotamer library including all conformations of side chains of lysine (for descriptor "C"), and tryptophan and phenylalanine (for descriptors "A" and "B"). The addition of these substituents to the backbone attachment points produces a resultant super-structure containing all possible substituents.

For the present example, the resultant superstructure has a total of 150 substituents, representing all rotamers of the three side chains described above, at all possible backbone attachment points, in which each rotamer can interact with rotamers at all positions other than its own. This represents a total of 7.6 * $10^{10}$ possible combinations. Preferably, in step 5, all atoms or pseudo-atoms that match the requirements of the pharmacophore are assigned to a descriptor type. For example any aromatic ring can be assigned the type "aromatic ring", rather than a particular descriptor, such as pharmacophore descriptor "A", since there may be a plurality of descriptors of a particular type in the pharmacophore. Thus, the assignment of a specific identity to an atom or pseudo-atom is preferably performed at a later stage. In this example, all six backbone atoms are assigned to the type "Cα", which includes pharmacophore descriptors "D", "E", and "F". The aromatic rings of tryptophan and phenylalanine and sidechain nitrogen of lysine are also preferably assigned according to their respective types, rather than to specific pharmacophore descriptors.

In steps 6 through 17 the resultant super-structures are subject to a filtration process, to eliminate rotamers from the super-structures, which are incompatible with the pharmacophore. Preferably, the filtration process is first performed by examining all possible pairs of rotamers, for greater efficiency, and then by examining all possible triplets of rotamer, to determine more complex relationships on a reduced set of rotamers. If necessary, the filtration process proceeds to higher order n-plets. More preferably, each filter of the filtration process is applied iteratively, most preferably until no further rotamers can be eliminated. The iterative application is preferred since the elimination of one rotamer from the pharmacophore may lead to the subsequent elimination of other rotamers, based upon a rotamer-rotamer interaction, which had not been previously independently eliminated during the filtration process.

Preferably, the process of elimination is performed by comparing the distances between descriptor centers on the super-structures to the corresponding distance in the pharmacophore. This comparison is performed with a preset relative tolerance, in order to correct for inaccuracies resulting from the use of a discrete set of conformations of the substituents and scaffolds. The tolerance factor is preferably determined empirically, and depends on the size and chemical nature of the scaffolds and pharmacophores. Thus two descriptors are defined as interacting if they are connected to different attachment points on the scaffold and the distance between them is within the tolerance level to the corresponding distance in the pharmacophore.

Preferably, the filtration process includes the provision of several different numerical parameters of the pharmacophore, including the minimal number of descriptors on the backbone (MIN-SCAF-DSC). This minimum does not necessarily equal the total number of descriptors on the backbone due to the possibility of descriptors that may be on either the scaffold or the substituents. Another numerical parameter is the minimal number of descriptors on the substituents (MIN-SUB-DSC), which, due to the above reason, may not equal the total number of substituent descriptors.

Other preferred parameters include, but are not limited to, the number of descriptor types each descriptor interacts with (TYP-INT); the number of descriptors each descriptor interacts with (DSC-INT); and the minimal number of intra-scaffold descriptor interactions (MIN-SCAF-INT).

As shown, preferably the filtration process begins with step 6 in FIG. 2, in which rotamers that clash with the backbone are eliminated. In step 7, pairs of rotamers that clash with each other are marked. A clash may be defined in several ways, and in the present embodiment is defined as a situation in which the distance between any two atoms in the system is smaller than 80% of the sum of the van-der-Waals radii of the two atoms.

In step 8, the descriptor type assignments to the atoms of the backbone are examined to remove those descriptor assignments that are incompatible with the pharmacophore. Preferably, step 8 is performed iteratively until no further descriptor assignments can be eliminated. More preferably, step 8 further features the following steps. First, all possible descriptor identifies are recorded for each of the relevant atoms on the scaffold. In the example of FIG. 1A these atoms are the Cα atoms that can each be assigned the identities D, E and F. Then, each identity assignment is examined to determine the number of different on-scaffold positions with descriptors that fit within an allowed distance, and to determine the number of different descriptors associated with these pairs. Next, the number of different pairs is preferably compared to the minimal number of intra-scaffold interactions for the pharmacophore (MIN-SCAF-INT). The number of different descriptors associated with these pairs is compared to the minimal number of descriptors on the scaffold (MIN-SCAF-DSC). Next, those descriptor assignments that are incompatible with MIN-SCAF-INT and MIN-SCAF-DSC are preferably eliminated.

In step 9, preferably all possible combinations of descriptors on the scaffold are screened to check whether they form a full sub-pharmacophore with MIN-SCAF-DSC elements. This step is the only step in which compliance with a full sub-pharmacophore, namely the sub-pharmacophore that includes all on-scaffold descriptors, is required. Although this requires more computer resources than the filters that examine lower order combinations, it is restricted to the scaffold, and thus the number of possible options to examine is relatively very small. Descriptor assignments that do not comply with any full on-scaffold sub-pharmacophore are eliminated. Preferably if no descriptor assignments are left the scaffold is eliminated and the procedure returns to step 3 for examination of the next scaffold.

In step 10, a matrix of all pair-wise interactions between all remaining rotamers at all positions is constructed. Preferably, the functional form adopted for this interaction is a square well potential with −1 for interacting combinations of rotamers and zero otherwise.

In step 11, the rotamers are filtered according to the description types that each rotamer interacts with. This is a simple and rapid, yet highly effective filter. Preferably, the following parameters are determined for each rotamer: (a) the number of different on-scaffold descriptors with which the rotamer interacts; (b) the number of different rotamer-positions which contain other rotamers with which the rotamer interacts; and (c) the total number of different descriptor types associated with these pairs.

Next, for each rotamer the above parameters (a), (b) and (c) are compared respectively to MIN-SCAF-DSC, MIN-SUB-DSC and TYP-INT. Rotamers that cannot satisfy these constraints are eliminated. The number of different rotamer-positions that contain other rotamers with which the rotamer interacts, as well as the number of descriptor types associated with these rotamer pairs, is examined to ensure that a given rotamer does not interact with two different rotamers in the same position, thereby satisfying TYP-INT without being compatible with the pharmacophore.

In step 12, the rotamers are filtered according to descriptor identities. This step is a refinement of the previous step, step 11, except that pharmacophore descriptors are now given specific identities rather than being examined as descriptor types. For example, each descriptor, which was previously identified as an aromatic ring, is now recalculated once as descriptor "A" and once as descriptor "B". This step is able to refine the identity or identifies assigned to a rotamer by eliminating assignments that do not display the number of interactions required by the pharmacophore. Preferably in this step the following parameters are calculated for each descriptor assignment: (a) the number of different on-scaffold descriptors with which the rotamer interacts for each assignment; (b) the number of different rotamer-positions which contain other rotamers with which the rotamer interacts for each assignment; and (c) the total number of different descriptors associated with these pairs.

Next, for each descriptor center assignment for each rotamer the above parameters (a), (b) and (c) are compared respectively to MIN-SCAF-DSC, MIN-SUB-DSC and DSC-INT. Descriptor assignments that do not satisfy these constraints are eliminated. Rotamers for which no assignment remains are also eliminated.

In step 13, the backbone scaffold is examined again with all remaining rotamers, in order to eliminate additional on-scaffold descriptor assignments which are not compatible with the required parameters for the pharmacophore. Preferably, the number of different scaffold positions with which an on-scaffold descriptor interacts is determined for each on-scaffold descriptor. Next, the corresponding descriptors associated with these interactions are recorded. The number of different positions containing rotamers that interact with each on-scaffold descriptor is then determined. Finally, the number of different scaffold or rotamer descriptors with which each on-scaffold descriptor interacts is determined. In this step all descriptor identities incompatible with MIN-SCAF-DSC, MIN-SCAF-INT, MIN-SUB-DSC and DSC-INT are eliminated.

Next, preferably step 9 is repeated, i.e. all possible combinations of descriptors on the scaffold that form sub-pharmacophores with MIN-SCAF-DSC elements are identified and descriptor assignments that do not participate in any such combination are eliminated. If no descriptor assignments are left the scaffold is eliminated and the procedure returns to step 3 for examination of the next scaffold.

Preferably, in step 14, steps 12 and 13 are repeated until no additional rotamers or descriptor assignments are eliminated by these steps.

In step 15, the rotamers are preferably filtered according to triplets of descriptor types, more preferably until no further rotamers can be eliminated. The previous steps examined only pairs of descriptors, and as such may not have eliminated all rotamers that are incompatible with the pharmacophore. Progressing to higher order combinations of descriptors increases the chances of detecting incompatible rotamer combinations, albeit at the expense of larger computer resources. For this reason higher order combinations are checked only after the elimination of rotamers by the filters that use lower order combinations. A triplet (or a higher order n-plet) is considered interacting if all pairs that form the triplet (or n-plet) interact. The application of filters that use triplets preferably uses the following parameters: (a) the number of different pairs with which the rotamer interacts; (b) the number of different pairs of rotamer-positions which contain other rotamers with which the rotamer interacts; and (c) the total number of different descriptor types each rotamers interacts with.

Next, for each rotamer the above parameters (a), (b) and (c) are compared respectively to DSC-INT, MIN-SUB-DSC and TYP-INT. Rotamers that do not satisfy these constraints are eliminated.

In step 16, preferably steps 12–14 are repeated.

In step 17, preferably all physically realizable molecules that can be constructed from the remaining super-structures and attached substituents are generated, and each is checked systematically for the existence of the pharmacophore.

In step 18, the procedure returns to step 3 and is repeated for the next scaffold in the library.

Optionally and preferably, the method can be extended with more restrictive conditions for the triplets or by examining higher order combinations, or even with more sophisticated filters. Such extensions are optional for small pharmacophores, yet become necessary for larger ones in order to reduce the number of possible pharmacophore-presenting molecules to a number that is small enough to be scanned exhaustively for the presence of pharmacophore.

EXAMPLE 1

Results for the Pharmacophores of FIG. 1

The pharmacophores of FIG. 1, which are pharmacophores extracted from a group of known analogs of somatostatin, were used first to test the method of the present invention on a known analog (namely that depicted in FIG. 1), and then to determine one or more novel candidate molecules that display these pharmacophores. The former task required an examination of about $10^{11}$ combinations of rotamers for a single scaffold, namely the backbone of the analog depicted in FIG. 1. When performed on a Silicon Graphics R10000 195 MHz processor this examination took about 10 seconds, and resulted in the correct choice of positions and rotamers, thereby reproducing the active molecule.

For the latter task, a library of 940 scaffolds was used, featuring 94 different cyclic peptidomimetic backbones with 10 conformations for each. An order of $5 \times 10^{15}$ possibilities (different conformations of ca. $6 \times 10^5$ molecules) were scanned within 1.25 hours on a 32 processor TR2000 computer (Terra Computers, Israel) using the current version of the program, and identified 19 novel backbone scaffolds and corresponding substituents which displayed the somatostatin pharmacophore depicted in FIG. 1A.

These novel molecules are called backbone cyclized peptide analogs, as listed below wherein, XXX denotes any L-alpha amino acid, (D) denotes the D stereoisomer of the subsequent amino acid, and (NM) denotes an N-methylated amino acid. The sequences include amino acid analogs which are alkylated on the nitrogens of the peptide backbone, by alkyl groups which form bridging groups. These alkyl groups form bridges such that these cyclic peptide analogs are conformationally constrained. The terminology of these backbone cyclized peptidomimetics and the N alpha alkylated building units is as disclosed in WO 95/33765, incorporated herein in its entirety. These novel molecules are:

(SEQ ID NO 1) XXX(C1)-XXX-LYS-(NM)PHE-TRP(N2)-XXX-NH2
(SEQ ID NO 2) XXX(C1)-XXX-LYS-TRP-PHE-XXX(N3)-NH2
(SEQ ID NO 3) (D)XXX(C1)-(D)-XXX-(D)PRO-(D)PHE-(D)TRP-(D)-LYS(N2)-NH2
(SEQ ID NO 4) (D)XXX(C1)-(D)XXX-LYS-(D)TRP-(D)PHE-(D)XXX(N2)-NH2
(SEQ ID NO 5) (D)XXX(C1)-(D)XXX-LYS-(D)TRP-(D)PHE-(D)XXX(N3)-NH2
(SEQ ID NO 6) (D)XXX(C2)-(D)XXX-XXX-LYS-(D)TRP(N2)-(D)PHE-NH2
(SEQ ID NO 7) (D)XXX(C2)-(D)XXX-(D)TRP-(D)LYS-(D)XXX(N3)-(D)PHE-NH2
(SEQ ID NO 8) (D)XXX(N2)-(D)XXX-XXX-PHE-(D)TRP-(D)LYS(C3)-NH2
(SEQ ID NO 9) (D)XXX(N2)-(D)XXX-(D)LYS-(D)PHE-(D)XXX-(D)PHE(C2)-NH2
(SEQ ID NO 10) (D)XXX(N2)-(D)XXX-LYS-TRP-(D)PHE-(D)XXX(C3)-NH2
(SEQ ID NO 11) (D)LYS-(D)TRP(N2)-(D)XXX-(D)XXX-(D)XXX(C2)-(D)PHE-NH2
(SEQ ID NO 12) (D)LYS(C1)-TRP-(D)PHE-(D)XXX-(D)XXX-(D)XXX(N3)-(D)XXX-NH2
(SEQ ID NO 13) (D)LYS(N3)-(D)TRP-(D)PHE-(D)XXX-(D)XXX-(D)XXX(C2)-NH2
(SEQ ID NO 14) (D)PHE(C2)-(D)LYS-XXX-(D)XXX-(D)XXX(N2)-(D)PHE-NH2
(SEQ ID NO 15) LYS(C1)-(D)TRP-(D)PHE-XXX(N3)-XXX-XXX-NH2
(SEQ ID NO 16) LYS(C2)-TRP-(D)PHE-XXX-XXX(N2)-XXX-NH2
(SEQ ID NO 17) PHE(C2)-(NM)TRP-LYS-XXX-XXX-XXX(N3)-NH2
(SEQ ID NO 18) PHE(N2)-TRP-(D)LYS-XXX-XXX-XXX(C3)-NH2
(SEQ ID NO 19) PHE(N3)-TRP-LYS-XXX-XXX-XXX(C2)-NH2

Repeating the procedure using the pharmacophore of FIG. 1B resulted in 35 additional suggestions:

(SEQ ID NO 20) XXX(C1)-PHE-(D)TRP-LYS-XXX-XXX(N2)-NH2
(SEQ ID NO 21) XXX(C1)-PHE-(D)TRP-LYS-XXX-XXX(N2)-NH2
(SEQ ID NO 22) XXX(C1)-PHE-(D)TRP-LYS-XXX-XXX(N3)-NH2
(SEQ ID NO 23) XXX(C1)-PHE-(D)TRP-LYS-XXX-XXX(N3)-NH2
(SEQ ID NO 24) XXX(C2)-XXX-(D)PHE-(D)TRP-LYS(N2)-XXX-NH2
(SEQ ID NO 25) XXX(C2)-(NM)XXX-LYS-TRP-PHE-XXX(N3)-NH2
(SEQ ID NO 26) XXX(N2)-LYS-(D)TRP-PHE-XXX-XXX(C3)-NH2
(SEQ ID NO 27) XXX(N2)-LYS-(D)TRP-PHE-XXX(C3)-XXX-NH2
(SEQ ID NO 28) XXX(N2)-PHE-(D)TRP-(D)LYS-XXX-XXX(C3)-NH2
(SEQ ID NO 29) XXX(N2)-PHE-(D)TRP-LYS-XXX-XXX(C3)-NH2
(SEQ ID NO 30) (D)XXX(C1)-(D)LYS-(D)XXX-(D)(NM)XXX-(D)PHE(N2)-(D)TRP-NH2
(SEQ ID NO 31) (D)XXX(C1)-(D)LYS-(D)TRP-(D)(NM)XXX-(D)PHE(N2)-(D)XXX-NH2
(SEQ ID NO 32) (D)XXX(C1)-(D)(NM)LYS-(D)TRP-(D)XXX-(D)XXX-(D)PHE(N2)-NH2
(SEQ ID NO 33) (D)XXX(C2)-XXX-(D)PHE-(D)TRP(N2)-(D)LYS-NH2
(SEQ ID NO 34) (D)XXX(C2)-(D)PHE-(D)TRP-(D)LYS(N3)-(D)XXX-(D)XXX-(D)XXX-NH2
(SEQ ID NO 35) (D)XXX(C2)-(D)TRP-(D)LYS-(D)XXX-(D)XXX(N3)-(D)PHE-NH2
(SEQ ID NO 36) (D)XXX(C3)-(D)PHE-(D)XXX-(D)TRP-(D)LYS(N2)-(D)XXX-NH2
(SEQ ID NO 37) (D)XXX(C3)-(D)TRP-(D)LYS-(D)XXX-(D)XXX(N2)-(D)PHE-NH2
(SEQ ID NO 38) (D)XXX(N2)-(D)LYS-TRP-(D)XXX-(D)PHE(C3)-(D)XXX-NH2
(SEQ ID NO 39) (D)XXX(N2)-(D)LYS-TRP-(D)PHE-(D)XXX(C3)-(D)XXX-NH2
(SEQ ID NO 40) (D)LYS(C1)-(D)XXX-(D)XXX-(D)PHE(N2)-(D)TRP-NH2
(SEQ ID NO 41) (D)LYS(C1)-(D)XXX-(D)PRO-(D)PHE(N2)-(D)TRP-NH2
(SEQ ID NO 42) (D)TRP(C2)-(D)LYS-(D)XXX-(D)XXX-(D)XXX-(D)PHE(N3)-NH2
(SEQ ID NO 43) (D)TRP(C2)-(D)PHE-(D)(NM)XXX-(D)XXX-(D)LYS(N3)-(D)XXX-NH2
(SEQ ID NO 44) LYS(C1)-TRP-XXX-TRP-XXX-XXX(N3)-NH2
(SEQ ID NO 45) LYS(C1)-TRP-(D)PHE-(D)XXX(N2)-XXX-NH2
(SEQ ID NO 46) LYS(C3)-TRP-XXX-XXX-XXX(N2)-PHE-NH2
(SEQ ID NO 47) LYS(N2)-XXX-(D)XXX-XXX-PHE(C3)-TRP-NH2
(SEQ ID NO 48) LYS(N2)-XXX-PRO-PHE(C3)-TRP-NH2
(SEQ ID NO 49) LYS(N2)-GLY-PRO-TRP(C3)-XXX-TRP-NH2
(SEQ ID NO 50) LYS(N2)-TRP-XXX-XXX-XXX(C2)-PHE-NH2
(SEQ ID NO 51) LYS(N2)-TRP-(D)XXX-(D)PHE(C3)-XXX-NH2
(SEQ ID NO 52) PHE(C1)-TRP-(D)LYS-XXX-XXX-XXX(N3)-NH2
(SEQ ID NO 53) TRP(C1)-(NM)XXX-XXX-LYS-TRP-XXX(N2)-NH2
(SEQ ID NO 54) TRP(C3)-LYS-XXX-XXX-PHE(N2)-XXX-NH2

Thus, the method of the present invention was shown to be highly effective and efficient to select suitable molecules according to a pharmacophore, a virtual library of scaffolds and a virtual library of substituents.

EXAMPLE 2

Figure 3:
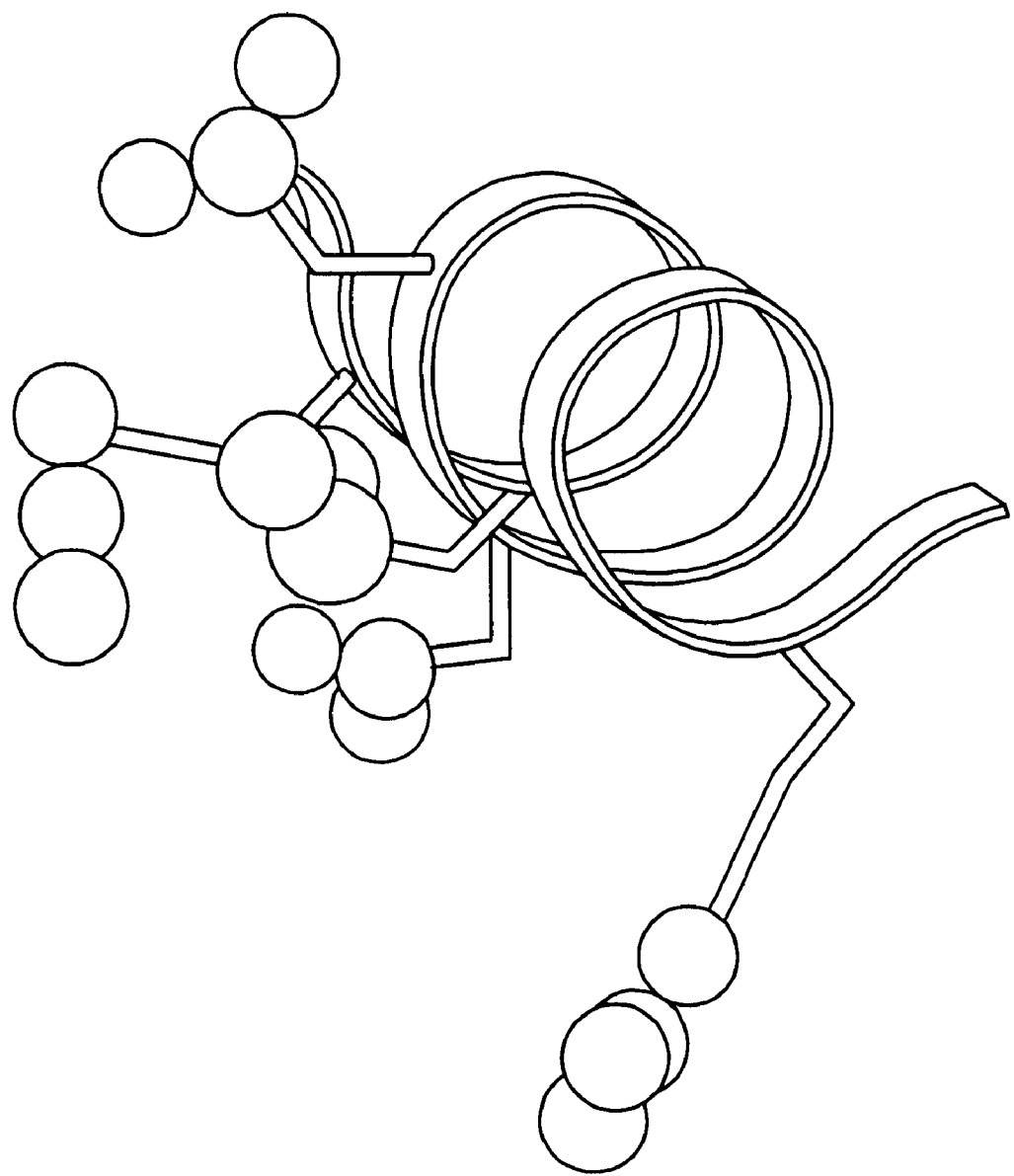
FIG. 3 shows the structural motif of the receptor-binding helix of Growth Hormone, in which the relevant pharmacophore descriptor centers are highlighted by circles.

Results for the Pharmacophore Extracted from a Receptor-binding Helix of Growth-Hormone Human Growth Hormone (hGH) binds to the membrane bound hGH receptor. The three-dimensional structure of a complex of this hormone with its receptor has been determined crystallographically. From this structure the contact regions between the hormone and receptor can be deducted. One of these regions is provided by a single face of Helix-1 of the 4 helical hormone. Based on an energetic analysis of the interaction of this helix with the receptor we deduced a structural motif, highlighted in FIG. 3. The virtual scaffold library described in Example 1 was screened for the motif on the TERRA 2000. A total of ca. $2 \times 10^{16}$ combinations of scaffolds and sidechains were screened within 1 hour and 50 minutes, and resulted in the elucidation of 24 novel molecules that display the desired motif. Again the definitions are appear in Example 1. These molecules are:

(SEQ ID NO 55) XXX(C2)-ARG-(D)ASN-(D)ARG-GLU(N2)-VAL-NH2
(SEQ ID NO 56) XXX(C2)-ARG-(NM)-GLN-ARG-GLU(N2)-VAL-NH2
(SEQ ID NO 57) XXX(C2)-(D)ARG-ASN-(D)ARG-GLU(N2)-ALA-NH2
(SEQ ID NO 58) XXX(N2)-(D)ASP-(D)-ARG-(D)ASN(C2)-(D)ARG-(D)LEU-NH2
(SEQ ID NO 59) ARG-VAL(N2)-ARG-GLU-XXX(C2)-ASN-NH2
(SEQ ID NO 60) ARG(C1)-ASN-ARG-GLU(N2)-ALA-NH2
(SEQ ID NO 61) ARG(C1)-(D)GLN-(D)GLU-LEU(N3)-ARG-XXX-NH2
(SEQ ID NO 62) ARG(C1)-(D)VAL-(D)GLU-ARG(N2)-ASN-XXX-NH2
(SEQ ID NO 63) ARG(C1)-GLN-(D)ARG-LEU(N2)-GLU-NH2
(SEQ ID NO 64) ARG(C2)-ASN-ARG-GLU(N2)-LEU-NH2
(SEQ ID NO 65) ARG(C2)-(D)ASN-ARG-GLU(N2)-VAL-NH2
(SEQ ID NO 66) ARG(N2)-(D)GLN-ARG-(D)GLU-LEU(C2)-NH2
(SEQ ID NO 67) ARG(N2)-GLN-ARG-GLU-VAL(C3)-NH2
(SEQ ID NO 68) (D)XXX-(D)ARG(N2)-(D)GLU-(D)ARG-(D)GLU(C2)-(D)ALA-NH2
(SEQ ID NO 69) (D)XXX(N2)-(D)LEU-(D)ASP-(D)ARG(C2)-(D)GLN-(D)ARG-NH2
(SEQ ID NO 70) (D)ARG(C1)-(D)ASN-(D)ARG-(D)(NM)GLU-(D)XXX(N2)-(D)VAL-NH2
(SEQ ID NO 71) (D)ARG(C1)-(D)GLN-(D)ARG-(D)GLU(N2)-(D)VAL-(D)XXX-NH2
(SEQ ID NO 72) (D)ARG(C2)-(D)GLN-(D)(NM)ARG-(D)GLU-(D)XXX(N3)-(D)VAL-NH2
(SEQ ID NO 73) (D)ARG(N2)-(D)ALA-(D)PRO-(D)GLU-(D)ARG-(D)ASN(C3)-NH2
(SEQ ID NO 74) (D)ARG(N2)-(D)GLN-(D)XXX-(D)ASP(C2)-(D)VAL-(D)ARG-NH2
(SEQ ID NO 75) (D)ARG(N2)-(D)GLN-(D)ARG-(D)ASP(C2)-(D)VAL-(D)XXX-NH2
(SEQ ID NO 76) (D)ARG(N2)-VAL-XXX-GLN(C2)-ARG-GLU-NH2
(SEQ ID NO 77) GLN(C1)-(D)ARG-(D)XXX-GLU(N3)-LEU-ARG-NH2
(SEQ ID NO 78) GLU(N2)-(NM)GLN-XXX-ARG(C2)-LEU-ARG-NH2

Four of these molecules are depicted in FIG. 4, superimposed on the growth hormone helix. It can clearly be seen that for each of the four molecules the five sidechains that comprise the pharmacophore overlap well with those presented by the helix.

While the invention has been described with respect to the limited number of embodiments, it will be appreciated that many variations, modifications and other applications of the invention may be made.

What is claimed is:

1. A method for identifying at least one molecule fitting the constraints imposed by a pharmacophore, each of the constraints of the pharmacophore being defined by at least one pharmacophore parameter, the steps of the method being performed by a data processor, the method comprising the steps of:
   (a) providing a first virtual library of at least one scaffold, each scaffold containing at least one attachment point for a substituent, each scaffold including a plurality of atoms, such that said scaffold is defined by a set of three-dimensional coordinates for each atom of said scaffold;
   (b) providing a second virtual library of a plurality of substituents, each of said plurality of substituents being described by a set of physically realizable discrete conformations, wherein each conformation of each of said plurality of substituents is a rotamer;
   (c) concurrently adding all rotamers from said second virtual library to each attachment point of each scaffold to form at least one super-structure;
   (d) assigning pharmacophore descriptors to all possible groups of at least one atom on said rotamers and on said scaffold;
   (e) testing the compatibility of each rotamer in each super-structure with a pharmacophore parameter;
   (f) eliminating a specific rotamer if said specific rotamer cannot exist in at least one combination compatible with each pharmacophore parameter;
   (g) eliminating a specific scaffold if said scaffold descriptor assignments are not compatible with each pharmacophore parameter; and
   (h) identifying at least one physically realizable molecule from a combination of remaining rotamers and a remaining scaffold.

2. The method of claim 1, further comprising the step of:
   (i) selecting the at least one molecule if said at least one molecule displays the pharmacophore.

3. The method of claim 2, wherein step (e) includes the step of applying at least one filter to each super-structure.

4. The method of claim 1, wherein the at least one pharmacophore parameter includes a plurality of pairs of pharmacophore descriptors, and wherein step (d) further comprises the step of creating a matrix of all distances between all possible pairs of pharmacophore descriptors.

5. The method of claim 1, wherein said at least one scaffold is peptidic.

6. The method of claim 5, wherein each type of a pharmacophore descriptor is selected from the group consisting of an atom, a group of atoms and a pseudoatom.

7. The method of claim 6, wherein said pharmacophore descriptor is selected from the group consisting of an entity contributed from said scaffold, an entity contributed from said plurality of substituents and an entity contributed from either said scaffold or said plurality of substituents.

8. The method of claim 7, wherein said pharmacophore parameter includes said pharmacophore descriptor and a relative position of said pharmacophore descriptor.

9. The method of claim 8, wherein step (e) further comprises the step of:
   (i) comparing each on-scaffold descriptor assignment to eliminate each scaffold being incompatible with said at least pharmacophore parameter, such that said combination is selected only if said scaffold features a full on-scaffold sub-pharmacophore.

10. The method of claim 9, wherein step (i) further comprises the steps of:
   (1) recording all possible descriptor identities for each group of at least one on-scaffold atom;
   (2) examining each descriptor identity to determine a number of different positions on the scaffold with descriptor pairs within an allowed distance;
   (3) determining a number of said descriptor pairs and a number of different descriptors associated with each descriptor pair;
   (4) comparing said number of said descriptor pairs to a minimal number of intra-scaffold interactions for the pharmacophore (MIN-SCAF-INT), wherein MIN-SCAF-INT is defined as a pharmacophore parameter;

(5) comparing said number of different descriptors associated with each descriptor pair to a minimal number of descriptors on the scaffold (MIN-SCAF-DSC), wherein MIN-SCAF-DSC is defined as a pharmacophore parameter; and (6) eliminating each descriptor assignment incompatible with MIN-SCAF-INT and MIN-SCAF-DSC.

11. The method of claim 10, wherein step (i) further comprises the steps of:

(7) examining all combinations of descriptors on the scaffold to determine whether each combination of descriptors forms a full sub-pharmacophore with MIN-SCAF-DSC elements, such that if said combination of descriptors does not form said full sub-pharmacophore, said combination of descriptors is eliminated.

12. The method of claim 9, wherein step (e) further comprises the steps of:

(ii) eliminating each rotamer if said rotamer is incompatible with said scaffold;

(iii) filtering all pairs of rotamers according to a pharmacophore descriptor type, such that if said pharmacophore descriptor type of said rotamers is incompatible with said at least one pharmacophore parameter, said rotamers are eliminated;

(iv) filtering all pairs of rotamers according to a pharmacophore descriptor position, such that if said pharmacophore descriptor position is incompatible with said at least one pharmacophore parameter, said rotamers are eliminated; and (v) comparing said scaffold to all remaining rotamers, such that if a remaining rotamer is incompatible with said scaffold, said remaining rotamer is eliminated.

13. The method of claim 12, wherein steps (iv) and (v) are repeated until no additional rotamers are eliminated.

14. The method of claim 13, wherein step (e) further comprises the step of:

(vi) filtering all triplets of rotamers according to said pharmacophore descriptor type, such that if said pharmacophore descriptor type of said rotamers is incompatible with said at least one pharmacophore parameter, said rotamers are eliminated.

15. The method of claim 14, wherein step (e) further comprises the step of repeating steps (iii) to (v).

16. The method of claim 12, wherein step (e) further comprises the steps of:

(vi) constructing a matrix of all distances between each pair of rotamers;

(vii) comparing said distance between said pair of rotamers to a corresponding distance between said pair of pharmacophore descriptors in the pharmacophore; and (viii) eliminating said pair of rotamers if said distance between said pair of rotamers is within said corresponding distance between said pair of pharmacophore descriptors plus a tolerance factor.

17. The method of claim 12, wherein step (e) further comprises the steps of:

(vi) determining a number of different descriptors of the scaffold with which each rotamer interacts;

(vii) comparing said scaffold descriptor number to a minimal number of descriptors on the scaffold (MIN-SCAF-DSC); and (viii) eliminating said rotamer if said scaffold descriptor number is less than said MIN-SCAF-DSC.

18. The method of claim 12, wherein step (e) further comprises the steps of:

(vi) determining a rotamer number of other rotamers with which each rotamer interacts;

(vii) comparing said rotamer number to a minimal number of descriptors on the substituents (MIN-SUB-DSC) wherein MIN-SUB-DSC is defined as a pharmacophore parameter; and (viii) eliminating said rotamer if said rotamer number is less than said MIN-SUB-DSC.

19. The method of claim 12, wherein step (e) further comprises the steps of:

(vi) determining a total descriptor number of a total number of different descriptors associated with each pair of rotamers;

(vii) comparing said total descriptor number to a number of descriptor types with which each descriptor interacts (TYP-INT), wherein TYP-INT is defined as a pharmacophore parameter; and (viii) eliminating said rotamer if said total descriptor number is less than said TYP-INT.

20. A method for identifying at least one molecule fitting the constraints imposed by a pharmacophore, the pharmacophore featuring at least one pharmacophore parameter, each of the constraints of the pharmacophore being defined by at least one pharmacophore parameter, the steps of the method being performed by a data processor, the method comprising the steps of:

(a) providing a first virtual library of at least one scaffold, each scaffold containing at least one attachment point for a substituent, each scaffold including a plurality of atoms, such that said scaffold is defined by a set of three-dimensional coordinates for each atoms of said scaffold;

(b) providing a second virtual library of a plurality of substituents, each of said plurality of substituents being described by a set of physically realizable discrete conformations, wherein each conformation of each of said plurality of substituents is a rotamer;

(c) concurrently adding all rotamers from said second virtual library to each attachment point of each scaffold to form each super-structure;

(d) assigning pharmacophore descriptors to all possible groups of at least one atom on said rotamers and on said scaffold;

(e) creating a matrix of all distances between all possible pairs of pharmacophore descriptors;

(f) comparing a rotamer distance between each pair of rotamer descriptors on said scaffold to a pharmacophore distance between said pair of pharmacophore descriptors;

(g) rejecting said pair of rotamers if said rotamer distance is incompatible with said pharmacophore distance;

(h) eliminating each rotamer if said rotamer is incompatible with said scaffold;

(i) filtering all pairs of rotamers according to a pharmacophore descriptor type, such that if said pharmacophore descriptor type of said rotamers is incompatible with said at least one pharmacophore parameter, said rotamers are eliminated;

(j) filtering all pairs of rotamers according to a pharmacophore descriptor position, such that if said pharmacophore descriptor position is incompatible with said at least one pharmacophore parameter, said rotamers are eliminated;

(k) recording all possible descriptor identities for each atom on the scaffold;

(l) examining each descriptor identity to determine a number of different positions on the scaffold with descriptor pairs within an allowed distance;

(m) determining a number of said descriptor pairs and a number of different descriptors associated with each descriptor pair;

(n) comparing said number of said descriptor pairs to a minimal number of intra-scaffold interactions for the pharmacophore (MIN-SCAF-INT), wherein MIN-SCAF-INT is defined as a pharmacophore parameter;

(o) comparing said number of different descriptors associated with each descriptor pair to a minimal number of descriptors on the scaffold (MIN-SCAF-DSC), wherein MIN-SCAF-DSC is defined as a pharmacophore parameter;

(p) eliminating each descriptor assignment incompatible with MIN-SCAF-INT and MIN-SCAF-DSC;

(q) examining all combinations of descriptors on the scaffold to determine whether each combination of descriptors forms a full sub-pharmacophore with MIN-SCAF-DSC elements, such that if said combination of descriptors does not form said full sub-pharmacophore, said combination of descriptors is eliminated;

(r) determining a scaffold descriptor number of different descriptors of the scaffold with which each rotamer interacts;

(s) comparing said scaffold descriptor number to a minimal number of descriptors on the scaffold (MIN-SCAF-DSC), wherein MIN-SCAF-DSC is defined as a pharmacophore parameter; and (t) eliminating said rotamer if said scaffold descriptor number is less than said MIN-SCAF-DSC;

(u) determining a rotamer numbers of other rotamers with which each rotamer interacts;

(v) comparing said rotamer number to a minimal number of descriptors on said rotamer (MIN-SUB-DSC), wherein MIN-SUB-DSC is defined as a pharmacophore parameter;

(w) eliminating said rotamer if said rotamer number is less than said MIN-SUB-DSC;

(x) determining a total descriptor number of a total number of different descriptors associated with each pair of rotamers;

(y) comparing said total descriptor number to a number of descriptor types with which each descriptor interacts (TYP-INT), wherein TYP-INT is defined as a pharmacophore parameter;

(z) eliminating said rotamer if said total descriptor number is less than said TYP-INT;

(aa) comparing said scaffold to all remaining rotamers, such that if a remaining rotamer is incompatible with said scaffold, said remaining rotamer is eliminated;

(bb) eliminating a specific rotamer if said specific rotamer cannot exist in at least one rotamer combination compatible with each pharmacophore parameter;

(cc) eliminating said scaffold if said super-structure is not compatible with each pharmacophore parameter;

(dd) repeating steps (l) to (cc) until no additional rotamers are eliminated; and (ee) constructing the at least one molecule from a combination of remaining rotamers and a remaining scaffold.

21. A method for identifying at least one molecule having the constraints imposed by a pharmacophore, each of these constraints being defined by at least one pharmacophore parameter, the steps of the method being performed by a data processor, the method comprising the steps of:

(a) providing a first virtual library of at least one scaffold, each scaffold containing at least one attachment point for a substituent, and a set of three-dimensional coordinates for each atom of said scaffold;

(b) providing a second virtual library of a plurality of substituents, each of said plurality of substituents being described by a set of physically realizable discrete conformations, wherein each conformation of each of said plurality of substituents is a rotamer;

(c) concurrently adding all rotamers from said second virtual library to each attachment point of each scaffold to form the super-structures;

(d) assigning pharmacophore descriptors to all possible atoms or groups of atoms on the rotamers and on the scaffolds;

(e) applying a series of filters to each super-structure to test the compatibility of each rotamer in the super-structure to a pharmacophore parameter;

(f) eliminating any rotamer if said specific rotamer cannot exist in at least one combination that is compatible with all pharmacophore parameters;

(g) constructing molecules from combinations of remaining rotamers and scaffold; and (h) selecting those combinations that display the pharmacophore.

22. A method for identifying at least one molecule fitting the constraints imposed by a pharmacophore, each of the constraints of the pharmacophore being defined by at least one pharmacophore parameter, the steps of the method being performed by a data processor, the method comprising the steps of:

(a) providing a first virtual library of at least one scaffold, each scaffold containing at least one attachment point for a substituent, each scaffold including a plurality of atoms, such that said scaffold is defined by a set of three-dimensional coordinates for each atom of said scaffold;

(b) providing a second virtual library of a plurality of substituents, each of said plurality of substituents being described by a set of physically realizable discrete conformations, wherein each conformation of each of said plurality of substituents is a rotamer;

(c) concurrently adding all rotamers from said second virtual library to each attachment point of each scaffold to form at least one super-structure;

(d) assigning pharmacophore descriptors to all possible groups of at least one atom on said rotamers and on said scaffold;

(e) testing the compatibility of each rotamer in each super-structure with a pharmacophore parameter;

(f) eliminating a specific rotamer if said specific rotamer cannot exist in at least one combination compatible with each pharmacophore parameter;

(g) eliminating a specific scaffold if said scaffold descriptor assignments are not compatible with each pharmacophore parameter; and (h) identifying at least one physically realizable molecule from a combination of remaining rotamers and a remaining scaffold.

* * * * *

SEQUENCE LISTING

```
<160> NUMBER OF SEQ ID NOS: 78

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any L-alpha amino acid, modified residue
      = N-acylated amino acid
<221> NAME/KEY:
<222> LOCATION: (2)
<223> OTHER INFORMATION: Xaa = any L-alpha amino acid
<221> NAME/KEY: MOD_RES
<222> LOCATION: (5)
<223> OTHER INFORMATION: modified residue = N-acylated amino acid
<221> NAME/KEY:
<222> LOCATION: (6)
<223> OTHER INFORMATION: Xaa = any L-alpha amino acid

<400> SEQUENCE: 1
```

Xaa Xaa Lys Phe Trp Xaa
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any L-alpha amino acid, modified residue
      = N-acylated amino acid
<221> NAME/KEY:
<222> LOCATION: (2)
<223> OTHER INFORMATION: Xaa = any L-alpha amino acid
<221> NAME/KEY: MOD_RES
<222> LOCATION: (6)
<223> OTHER INFORMATION: modified residue = N-acylated amino acid

<400> SEQUENCE: 2

Xaa Xaa Lys Trp Phe Xaa
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY:
<222> LOCATION: (2)
<223> OTHER INFORMATION: Xaa = any D-alpha amino acid
<221> NAME/KEY: MOD_RES
<222> LOCATION: (6)
<223> OTHER INFORMATION: modified residue = N-acylated amino acid

<400> SEQUENCE: 3

Xaa Xaa Pro Phe Trp Lys
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY:
<222> LOCATION: (2)
<223> OTHER INFORMATION: Xaa = any D-alpha amino acid
<221> NAME/KEY: MOD_RES
<222> LOCATION: (6)
<223> OTHER INFORMATION: Xaa = any D-alpha amino acid, modified residue
      = N-acylated amino acid

<400> SEQUENCE: 4

Xaa Xaa Lys Trp Phe Xaa
 1               5

<210> SEQ ID NO 5

```
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY:
<222> LOCATION: (2)
<223> OTHER INFORMATION: Xaa = any D-alpha amino acid
<221> NAME/KEY: MOD_RES
<222> LOCATION: (6)
<223> OTHER INFORMATION: Xaa = any D-alpha amino acid, modified residue
      = N-acylated amino acid

<400> SEQUENCE: 5

Xaa Xaa Lys Trp Phe Xaa
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY:
<222> LOCATION: (2)
<223> OTHER INFORMATION: Xaa = any D-alpha amino acid
<221> NAME/KEY:
<222> LOCATION: (3)
<223> OTHER INFORMATION: Xaa = any L-alpha amino acid
<221> NAME/KEY: MOD_RES
<222> LOCATION: (5)
<223> OTHER INFORMATION: modified residue = N-acylated amino acid

<400> SEQUENCE: 6

Xaa Xaa Xaa Lys Trp Phe
 1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY:
<222> LOCATION: (2)
<223> OTHER INFORMATION: Xaa = any D-alpha amino acid
<221> NAME/KEY: MOD_RES
<222> LOCATION: (5)
<223> OTHER INFORMATION: Xaa = any D-alpha amino acid, modified residue
      = N-acylated amino acid

<400> SEQUENCE: 7

Xaa Xaa Trp Lys Xaa Phe
 1               5

<210> SEQ ID NO 8
<211> LENGTH: 6
<212> TYPE: PRT
```

```
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY:
<222> LOCATION: (2)
<223> OTHER INFORMATION: Xaa = any D-alpha amino acid
<221> NAME/KEY:
<222> LOCATION: (3)
<223> OTHER INFORMATION: Xaa = any L-alpha amino acid
<221> NAME/KEY: MOD_RES
<222> LOCATION: (6)
<223> OTHER INFORMATION: modified residue = N-acylated amino acid

<400> SEQUENCE: 8

Xaa Xaa Xaa Phe Trp Lys
 1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY:
<222> LOCATION: (2)
<223> OTHER INFORMATION: Xaa = any D-alpha amino acid
<221> NAME/KEY:
<222> LOCATION: (5)
<223> OTHER INFORMATION: Xaa = any D-alpha amino acid
<221> NAME/KEY: MOD_RES
<222> LOCATION: (6)
<223> OTHER INFORMATION: modified residue = N-acylated amino acid

<400> SEQUENCE: 9

Xaa Xaa Lys Phe Xaa Phe
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY:
<222> LOCATION: (2)
<223> OTHER INFORMATION: Xaa = any D-alpha amino acid
<221> NAME/KEY: MOD_RES
<222> LOCATION: (6)
<223> OTHER INFORMATION: Xaa = any D-alpha amino acid, modified residue
      = N-acylated amino acid

<400> SEQUENCE: 10

Xaa Xaa Lys Trp Phe Xaa
 1               5

<210> SEQ ID NO 11
<211> LENGTH: 6
<212> TYPE: PRT
```

```
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (2)
<223> OTHER INFORMATION: modified residue = N-acylated amino acid
<221> NAME/KEY:
<222> LOCATION: (3)
<223> OTHER INFORMATION: Xaa = any D-alpha amino acid
<221> NAME/KEY:
<222> LOCATION: (4)
<223> OTHER INFORMATION: Xaa = any D-alpha amino acid
<221> NAME/KEY: MOD_RES
<222> LOCATION: (5)
<223> OTHER INFORMATION: Xaa = any D-alpha amino acid, modified residue
      = N-acylated amino acid

<400> SEQUENCE: 11

Lys Trp Xaa Xaa Xaa Phe
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (4)
<223> OTHER INFORMATION: Xaa = any D-alpha amino acid
<221> NAME/KEY: MOD_RES
<222> LOCATION: (5)
<223> OTHER INFORMATION: Xaa = any D-alpha amino acid, modified residue
      = N-acylated amino acid
<221> NAME/KEY:
<222> LOCATION: (6)
<223> OTHER INFORMATION: Xaa = any D-alpha amino acid

<400> SEQUENCE: 12

Lys Trp Phe Xaa Xaa Xaa
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (4)
<223> OTHER INFORMATION: Xaa = any D-alpha amino acid
<221> NAME/KEY:
<222> LOCATION: (5)
<223> OTHER INFORMATION: Xaa = any D-alpha amino acid
<221> NAME/KEY: MOD_RES
<222> LOCATION: (6)
<223> OTHER INFORMATION: Xaa = any D-alpha amino acid, modified residue
      = N-acylated amino acid

<400> SEQUENCE: 13

Lys Trp Phe Xaa Xaa Xaa
 1               5

<210> SEQ ID NO 14
```

```
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (3)
<223> OTHER INFORMATION: Xaa = any L-alpha amino acid
<221> NAME/KEY:
<222> LOCATION: (4)
<223> OTHER INFORMATION: Xaa = any D-alpha amino acid
<221> NAME/KEY: MOD_RES
<222> LOCATION: (5)
<223> OTHER INFORMATION: Xaa = any D-alpha amino acid, modified residue
      = N-acylated amino acid

<400> SEQUENCE: 14

Phe Lys Xaa Xaa Xaa Phe
 1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (4)
<223> OTHER INFORMATION: Xaa = any L-alpha amino acid, modified residue
      = N-acylated amino acid
<221> NAME/KEY:
<222> LOCATION: (5)
<223> OTHER INFORMATION: Xaa = any L-alpha amino acid
<221> NAME/KEY:
<222> LOCATION: (6)
<223> OTHER INFORMATION: Xaa = any L-alpha amino acid

<400> SEQUENCE: 15

Lys Trp Phe Xaa Xaa Xaa
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (4)
<223> OTHER INFORMATION: Xaa = any L-alpha amino acid
<221> NAME/KEY: MOD_RES
<222> LOCATION: (5)
<223> OTHER INFORMATION: Xaa = any L-alpha amino acid, modified residue
      = N-acylated amino acid
<221> NAME/KEY:
<222> LOCATION: (6)
<223> OTHER INFORMATION: Xaa = any L-alpha amino acid

<400> SEQUENCE: 16

Lys Trp Phe Xaa Xaa Xaa
 1               5
```

```
<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (2)
<223> OTHER INFORMATION: modified residue = N-methylated amino acid
<221> NAME/KEY:
<222> LOCATION: (4)
<223> OTHER INFORMATION: Xaa = any L-alpha amino acid
<221> NAME/KEY:
<222> LOCATION: (5)
<223> OTHER INFORMATION: Xaa = any L-alpha amino acid
<221> NAME/KEY: MOD_RES
<222> LOCATION: (6)
<223> OTHER INFORMATION: Xaa = any L-alpha amino acid, modified residue
      = N-acylated amino acid

<400> SEQUENCE: 17

Phe Trp Lys Xaa Xaa Xaa
  1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (4)
<223> OTHER INFORMATION: Xaa = any L-alpha amino acid
<221> NAME/KEY:
<222> LOCATION: (5)
<223> OTHER INFORMATION: Xaa = any L-alpha amino acid
<221> NAME/KEY: MOD_RES
<222> LOCATION: (6)
<223> OTHER INFORMATION: Xaa = any L-alpha amino acid, modified residue
      = N-acylated amino acid

<400> SEQUENCE: 18

Phe Trp Lys Xaa Xaa Xaa
  1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (4)
<223> OTHER INFORMATION: Xaa = any L-alpha amino acid
<221> NAME/KEY:
<222> LOCATION: (5)
<223> OTHER INFORMATION: Xaa = any L-alpha amino acid
<221> NAME/KEY: MOD_RES
<222> LOCATION: (6)
<223> OTHER INFORMATION: modified residue = N-acylated amino acid

<400> SEQUENCE: 19
```

Phe Trp Lys Xaa Xaa Xaa
 1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any L-alpha amino acid, modified residue
      = N-acylated amino acid
<221> NAME/KEY:
<222> LOCATION: (5)
<223> OTHER INFORMATION: Xaa = any L-alpha amino acid
<221> NAME/KEY: MOD_RES
<222> LOCATION: (6)
<223> OTHER INFORMATION: Xaa = any L-alpha amino acid, modified residue
      = N-acylated amino acid

<400> SEQUENCE: 20

Xaa Phe Trp Lys Xaa Xaa
 1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any L-alpha amino acid, modified residue
      = N-acylated amino acid
<221> NAME/KEY:
<222> LOCATION: (5)
<223> OTHER INFORMATION: Xaa = any L-alpha amino acid
<221> NAME/KEY: MOD_RES
<222> LOCATION: (6)
<223> OTHER INFORMATION: Xaa = any L-alpha amino acid, modified residue
      = N-acylated amino acid

<400> SEQUENCE: 21

Xaa Phe Trp Lys Xaa Xaa
 1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any L-alpha amino acid, modified residue
      = N-acylated amino acid
<221> NAME/KEY:
<222> LOCATION: (5)
<223> OTHER INFORMATION: Xaa = any L-alpha amino acid
<221> NAME/KEY: MOD_RES
<222> LOCATION: (6)
<223> OTHER INFORMATION: Xaa = any L-alpha amino acid, modified residue
      = N-acylated amino acid

<400> SEQUENCE: 22

Xaa Phe Trp Lys Xaa Xaa
 1               5

```
<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any L-alpha amino acid, modified residue
      = N-acylated amino acid
<221> NAME/KEY:
<222> LOCATION: (5)
<223> OTHER INFORMATION: Xaa = any L-alpha amino acid
<221> NAME/KEY: MOD_RES
<222> LOCATION: (6)
<223> OTHER INFORMATION: Xaa = any L-alpha amino acid, modified residue
      = N-acylated amino acid

<400> SEQUENCE: 23

Xaa Phe Trp Lys Xaa Xaa
 1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any L-alpha amino acid, modified residue
      = N-acylated amino acid
<221> NAME/KEY:
<222> LOCATION: (2)
<223> OTHER INFORMATION: Xaa = any L-alpha amino acid
<221> NAME/KEY: MOD_RES
<222> LOCATION: (5)
<223> OTHER INFORMATION: modified residue = N-acylated amino acid
<221> NAME/KEY:
<222> LOCATION: (6)
<223> OTHER INFORMATION: Xaa = any L-alpha amino acid

<400> SEQUENCE: 24

Xaa Xaa Phe Trp Lys Xaa
 1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any L-alpha amino acid, modified residue
      = N-acylated amino acid
<221> NAME/KEY: MOD_RES
<222> LOCATION: (2)
<223> OTHER INFORMATION: Xaa = any L-alpha amino acid, modified residue
      = N-methylated amino acid
<221> NAME/KEY: MOD_RES
<222> LOCATION: (6)
<223> OTHER INFORMATION: Xaa = any L-alpha amino acid, modified residue
      = N-acylated amino acid

<400> SEQUENCE: 25

Xaa Xaa Lys Trp Phe Xaa
 1               5
```

```
<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any L-alpha amino acid, modified residue
      = N-acylated amino acid
<221> NAME/KEY:
<222> LOCATION: (5)
<223> OTHER INFORMATION: Xaa = any L-alpha amino acid
<221> NAME/KEY: MOD_RES
<222> LOCATION: (6)
<223> OTHER INFORMATION: Xaa = any L-alpha amino acid, modified residue
      = N-acylated amino acid

<400> SEQUENCE: 26

Xaa Lys Trp Phe Xaa Xaa
 1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any L-alpha amino acid, modified residue
      = N-acylated amino acid
<221> NAME/KEY: MOD_RES
<222> LOCATION: (5)
<223> OTHER INFORMATION: Xaa = any L-alpha amino acid, modified residue
      = N-acylated amino acid
<221> NAME/KEY:
<222> LOCATION: (6)
<223> OTHER INFORMATION: Xaa = any L-alpha amino acid

<400> SEQUENCE: 27

Xaa Lys Trp Phe Xaa Xaa
 1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any L-alpha amino acid, modified residue
      = N-acylated amino acid
<221> NAME/KEY:
<222> LOCATION: (5)
<223> OTHER INFORMATION: Xaa = any L-alpha amino acid
<221> NAME/KEY: MOD_RES
<222> LOCATION: (6)
<223> OTHER INFORMATION: Xaa = any L-alpha amino acid, modified residue
      = N-acylated amino acid

<400> SEQUENCE: 28

Xaa Phe Trp Lys Xaa Xaa
 1               5

<210> SEQ ID NO 29
<211> LENGTH: 6
<212> TYPE: PRT
<213> ORGANISM: Artificial Sequence
```

```
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any L-alpha amino acid, modified residue
      = N-acylated amino acid
<221> NAME/KEY:
<222> LOCATION: (5)
<223> OTHER INFORMATION: Xaa = any L-alpha amino acid
<221> NAME/KEY: MOD_RES
<222> LOCATION: (6)
<223> OTHER INFORMATION: Xaa = any L-alpha amino acid, modified residue
      = N-acylated amino acid

<400> SEQUENCE: 29

Xaa Phe Trp Lys Xaa Xaa
  1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY:
<222> LOCATION: (3)
<223> OTHER INFORMATION: Xaa = any D-alpha amino acid
<221> NAME/KEY: MOD_RES
<222> LOCATION: (4)
<223> OTHER INFORMATION: Xaa = any L-alpha amino acid, modified residue
      = N-methylated amino acid
<221> NAME/KEY: MOD_RES
<222> LOCATION: (5)
<223> OTHER INFORMATION: modified residue = N-acylated amino acid

<400> SEQUENCE: 30

Xaa Lys Xaa Xaa Phe Trp
  1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY: MOD_RES
<222> LOCATION: (4)
<223> OTHER INFORMATION: Xaa = any L-alpha amino acid, modified residue
      = N-methylated amino acid
<221> NAME/KEY: MOD_RES
<222> LOCATION: (5)
<223> OTHER INFORMATION: modified residue = N-acylated amino acid
<221> NAME/KEY:
<222> LOCATION: (6)
<223> OTHER INFORMATION: Xaa = any D-alpha amino acid

<400> SEQUENCE: 31

Xaa Lys Trp Xaa Phe Xaa
  1               5

<210> SEQ ID NO 32
<211> LENGTH: 6
```

```
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY: MOD_RES
<222> LOCATION: (2)
<223> OTHER INFORMATION: modified residue = N-methylated amino acid
<221> NAME/KEY:
<222> LOCATION: (4)
<223> OTHER INFORMATION: Xaa = any D-alpha amino acid
<221> NAME/KEY:
<222> LOCATION: (5)
<223> OTHER INFORMATION: Xaa = any D-alpha amino acid
<221> NAME/KEY: MOD_RES
<222> LOCATION: (6)
<223> OTHER INFORMATION: modified residue = N-acylated amino acid

<400> SEQUENCE: 32

Xaa Lys Trp Xaa Xaa Phe
  1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY:
<222> LOCATION: (2)
<223> OTHER INFORMATION: Xaa = any L-alpha amino acid
<221> NAME/KEY: MOD_RES
<222> LOCATION: (4)
<223> OTHER INFORMATION: modified residue = N-acylated amino acid

<400> SEQUENCE: 33

Xaa Xaa Phe Trp Lys
  1           5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY: MOD_RES
<222> LOCATION: (4)
<223> OTHER INFORMATION: modified residue = N-acylated amino acid
<221> NAME/KEY:
<222> LOCATION: (5)
<223> OTHER INFORMATION: Xaa = any D-alpha amino acid
<221> NAME/KEY:
<222> LOCATION: (6)
<223> OTHER INFORMATION: Xaa = any D-alpha amino acid

<400> SEQUENCE: 34

Xaa Phe Trp Lys Xaa Xaa
  1               5
```

```
<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY:
<222> LOCATION: (4)
<223> OTHER INFORMATION: Xaa = any D-alpha amino acid
<221> NAME/KEY: MOD_RES
<222> LOCATION: (5)
<223> OTHER INFORMATION: Xaa = any D-alpha amino acid, modified residue
      = N-acylated amino acid

<400> SEQUENCE: 35

Xaa Trp Lys Xaa Xaa Phe
 1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY:
<222> LOCATION: (3)
<223> OTHER INFORMATION: Xaa = any D-alpha amino acid
<221> NAME/KEY: MOD_RES
<222> LOCATION: (5)
<223> OTHER INFORMATION: Xaa = any D-alpha amino acid, modified residue
      = N-acylated amino acid
<221> NAME/KEY:
<222> LOCATION: (6)
<223> OTHER INFORMATION: Xaa = any D-alpha amino acid

<400> SEQUENCE: 36

Xaa Phe Xaa Trp Lys Xaa
 1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY:
<222> LOCATION: (4)
<223> OTHER INFORMATION: Xaa = any D-alpha amino acid
<221> NAME/KEY: MOD_RES
<222> LOCATION: (5)
<223> OTHER INFORMATION: Xaa = any D-alpha amino acid, modified residue
      = N-acylated amino acid

<400> SEQUENCE: 37

Xaa Trp Lys Xaa Xaa Phe
 1               5

<210> SEQ ID NO 38
```

```
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY:
<222> LOCATION: (4)
<223> OTHER INFORMATION: Xaa = any D-alpha amino acid
<221> NAME/KEY: MOD_RES
<222> LOCATION: (5)
<223> OTHER INFORMATION: modified residue = N-acylated amino acid
<221> NAME/KEY:
<222> LOCATION: (6)
<223> OTHER INFORMATION: Xaa = any D-alpha amino acid

<400> SEQUENCE: 38

Xaa Lys Trp Xaa Phe Xaa
 1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY: MOD_RES
<222> LOCATION: (5)
<223> OTHER INFORMATION: Xaa = any D-alpha amino acid, modified residue
      = N-acylated amino acid
<221> NAME/KEY:
<222> LOCATION: (6)
<223> OTHER INFORMATION: Xaa = any D-alpha amino acid

<400> SEQUENCE: 39

Xaa Lys Trp Phe Xaa Xaa
 1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (2)
<223> OTHER INFORMATION: Xaa = any D-alpha amino acid
<221> NAME/KEY:
<222> LOCATION: (3)
<223> OTHER INFORMATION: Xaa = any D-alpha amino acid
<221> NAME/KEY: MOD_RES
<222> LOCATION: (4)
<223> OTHER INFORMATION: modified residue = N-acylated amino acid

<400> SEQUENCE: 40

Lys Xaa Xaa Phe Trp
 1               5

<210> SEQ ID NO 41
<211> LENGTH: 5
```

```
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (2)
<223> OTHER INFORMATION: Xaa = any D-alpha amino acid
<221> NAME/KEY: MOD_RES
<222> LOCATION: (4)
<223> OTHER INFORMATION: modified residue = N-acylated amino acid

<400> SEQUENCE: 41

Lys Xaa Pro Phe Trp
 1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (3)
<223> OTHER INFORMATION: Xaa = any D-alpha amino acid
<221> NAME/KEY:
<222> LOCATION: (4)
<223> OTHER INFORMATION: Xaa = any D-alpha amino acid
<221> NAME/KEY:
<222> LOCATION: (5)
<223> OTHER INFORMATION: Xaa = any D-alpha amino acid
<221> NAME/KEY: MOD_RES
<222> LOCATION: (6)
<223> OTHER INFORMATION: modified residue = N-acylated amino acid

<400> SEQUENCE: 42

Trp Lys Xaa Xaa Xaa Phe
 1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (3)
<223> OTHER INFORMATION: Xaa = any D-alpha amino acid, modified residue
      = N-methylated amino acid
<221> NAME/KEY:
<222> LOCATION: (4)
<223> OTHER INFORMATION: Xaa = any D-alpha amino acid
<221> NAME/KEY: MOD_RES
<222> LOCATION: (5)
<223> OTHER INFORMATION: modified residue = N-acylated amino acid
<221> NAME/KEY:
<222> LOCATION: (6)
<223> OTHER INFORMATION: Xaa = any D-alpha amino acid

<400> SEQUENCE: 43

Trp Phe Xaa Xaa Lys Xaa
 1               5
```

```
<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (3)
<223> OTHER INFORMATION: Xaa = any L-alpha amino acid
<221> NAME/KEY:
<222> LOCATION: (5)
<223> OTHER INFORMATION: Xaa = any L-alpha amino acid
<221> NAME/KEY: MOD_RES
<222> LOCATION: (6)
<223> OTHER INFORMATION: Xaa = any L-alpha amino acid, modified residue
      = N-acylated amino acid

<400> SEQUENCE: 44

Lys Trp Xaa Trp Xaa Xaa
 1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (4)
<223> OTHER INFORMATION: Xaa = any D-alpha amino acid, modified residue
      = N-acylated amino acid
<221> NAME/KEY:
<222> LOCATION: (5)
<223> OTHER INFORMATION: Xaa = any L-alpha amino acid

<400> SEQUENCE: 45

Lys Trp Phe Xaa Xaa
 1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (3)
<223> OTHER INFORMATION: Xaa = any L-alpha amino acid
<221> NAME/KEY:
<222> LOCATION: (4)
<223> OTHER INFORMATION: Xaa = any L-alpha amino acid
<221> NAME/KEY: MOD_RES
<222> LOCATION: (5)
<223> OTHER INFORMATION: Xaa = any L-alpha amino acid, modified residue
      = N-acylated amino acid

<400> SEQUENCE: 46

Lys Trp Xaa Xaa Xaa Phe
 1               5
```

```
<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (2)
<223> OTHER INFORMATION: Xaa = any L-alpha amino acid
<221> NAME/KEY:
<222> LOCATION: (3)
<223> OTHER INFORMATION: Xaa = any D-alpha amino acid
<221> NAME/KEY:
<222> LOCATION: (4)
<223> OTHER INFORMATION: Xaa = any L-alpha amino acid
<221> NAME/KEY: MOD_RES
<222> LOCATION: (5)
<223> OTHER INFORMATION: modified residue = N-acylated amino acid

<400> SEQUENCE: 47

Lys Xaa Xaa Xaa Phe Trp
 1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (2)
<223> OTHER INFORMATION: Xaa = any L-alpha amino acid
<221> NAME/KEY: MOD_RES
<222> LOCATION: (4)
<223> OTHER INFORMATION: modified residue = N-acylated amino acid

<400> SEQUENCE: 48

Lys Xaa Pro Phe Trp
 1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (4)
<223> OTHER INFORMATION: modified residue = N-acylated amino acid
<221> NAME/KEY:
<222> LOCATION: (5)
<223> OTHER INFORMATION: Xaa = any L-alpha amino acid

<400> SEQUENCE: 49

Lys Gly Pro Trp Xaa Trp
 1               5

<210> SEQ ID NO 50
<211> LENGTH: 6
<212> TYPE: PRT
<213> ORGANISM: Artificial Sequence
```

```
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (3)
<223> OTHER INFORMATION: Xaa = any L-alpha amino acid
<221> NAME/KEY:
<222> LOCATION: (4)
<223> OTHER INFORMATION: Xaa = any L-alpha amino acid
<221> NAME/KEY: MOD_RES
<222> LOCATION: (5)
<223> OTHER INFORMATION: Xaa = any L-alpha amino acid, modified residue
      = N-acylated amino acid

<400> SEQUENCE: 50

Lys Trp Xaa Xaa Xaa Phe
 1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (3)
<223> OTHER INFORMATION: Xaa = any D-alpha amino acid
<221> NAME/KEY: MOD_RES
<222> LOCATION: (4)
<223> OTHER INFORMATION: modified residue = N-acylated amino acid
<221> NAME/KEY:
<222> LOCATION: (5)
<223> OTHER INFORMATION: Xaa = any L-alpha amino acid

<400> SEQUENCE: 51

Lys Trp Xaa Phe Xaa
 1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (4)
<223> OTHER INFORMATION: Xaa = any L-alpha amino acid
<221> NAME/KEY:
<222> LOCATION: (5)
<223> OTHER INFORMATION: Xaa = any L-alpha amino acid
<221> NAME/KEY: MOD_RES
<222> LOCATION: (6)
<223> OTHER INFORMATION: Xaa = any L-alpha amino acid, modified residue
      = N-acylated amino acid

<400> SEQUENCE: 52

Phe Trp Lys Xaa Xaa Xaa
 1               5

<210> SEQ ID NO 53
<211> LENGTH: 6
<212> TYPE: PRT
```

```
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (2)
<223> OTHER INFORMATION: Xaa = any L-alpha amino acid, modified residue
      = N-methylated amino acid
<221> NAME/KEY:
<222> LOCATION: (3)
<223> OTHER INFORMATION: Xaa = any L-alpha amino acid
<221> NAME/KEY: MOD_RES
<222> LOCATION: (6)
<223> OTHER INFORMATION: Xaa = any L-alpha amino acid, modified residue
      = N-acylated amino acid

<400> SEQUENCE: 53

Trp Xaa Xaa Lys Trp Xaa
 1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (3)
<223> OTHER INFORMATION: Xaa = any L-alpha amino acid
<221> NAME/KEY:
<222> LOCATION: (4)
<223> OTHER INFORMATION: Xaa = any L-alpha amino acid
<221> NAME/KEY: MOD_RES
<222> LOCATION: (5)
<223> OTHER INFORMATION: modified residue = N-acylated amino acid
<221> NAME/KEY:
<222> LOCATION: (6)
<223> OTHER INFORMATION: Xaa = any L-alpha amino acid

<400> SEQUENCE: 54

Trp Lys Xaa Xaa Phe Xaa
 1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: Xaa = any D-alpha amino acid, modified residue
      = N-acylated amino acid
<221> NAME/KEY: MOD_RES
<222> LOCATION: (5)
<223> OTHER INFORMATION: modified residue = N-acylated amino acid

<400> SEQUENCE: 55

Xaa Arg Asn Arg Glu Val
 1               5

<210> SEQ ID NO 56
<211> LENGTH: 6
<212> TYPE: PRT
<213> ORGANISM: Artificial Sequence
```

```
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: any D-alpha amino acid, modified residue =
      N-acylated amino acid
<221> NAME/KEY: MOD_RES
<222> LOCATION: (3)
<223> OTHER INFORMATION: modified residue = N-methylated amino acid
<221> NAME/KEY: MOD_RES
<222> LOCATION: (5)
<223> OTHER INFORMATION: modified residue = N-acylated amino acid

<400> SEQUENCE: 56

Xaa Arg Gln Arg Glu Val
 1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: any D-alpha amino acid, modified residue =
      N-acylated amino acid
<221> NAME/KEY: MOD_RES
<222> LOCATION: (5)
<223> OTHER INFORMATION: modified residue = N-acylated amino acid

<400> SEQUENCE: 57

Xaa Arg Asn Arg Glu Ala
 1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: any D-alpha amino acid, modified residue =
      N-acylated amino acid
<221> NAME/KEY: MOD_RES
<222> LOCATION: (4)
<223> OTHER INFORMATION: modified residue = N-acylated amino acid

<400> SEQUENCE: 58

Xaa Asp Arg Asn Arg Leu
 1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (2)
<223> OTHER INFORMATION: modified residue = N-acylated amino acid
<221> NAME/KEY: MOD_RES
<222> LOCATION: (5)
<223> OTHER INFORMATION: any D-alpha amino acid, modified residue =
      N-acylated amino acid

<400> SEQUENCE: 59
```

Arg Val Arg Glu Xaa Asn
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (4)
<223> OTHER INFORMATION: modified residue = N-acylated amino acid

<400> SEQUENCE: 60

Arg Asn Arg Glu Ala
1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (4)
<223> OTHER INFORMATION: modified residue = N-acylated amino acid
<221> NAME/KEY:
<222> LOCATION: (6)
<223> OTHER INFORMATION: Xaa = any L-alpha amino acid

<400> SEQUENCE: 61

Arg Gln Glu Leu Arg Xaa
1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (4)
<223> OTHER INFORMATION: modified residue = N-acylated amino acid
<221> NAME/KEY:
<222> LOCATION: (6)
<223> OTHER INFORMATION: Xaa = any L-alpha amino acid

<400> SEQUENCE: 62

Arg Val Glu Arg Asn Xaa
1               5

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)

```
<223> OTHER INFORMATION: modified residue = N-acylated amino acid
<221> NAME/KEY: MOD_RES
<222> LOCATION: (4)
<223> OTHER INFORMATION: modified residue = N-acylated amino acid

<400> SEQUENCE: 63

Arg Gln Arg Leu Glu
 1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (4)
<223> OTHER INFORMATION: modified residue = N-acylated amino acid

<400> SEQUENCE: 64

Arg Asn Arg Glu Leu
 1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (4)
<223> OTHER INFORMATION: modified residue = N-acylated amino acid

<400> SEQUENCE: 65

Arg Asn Arg Glu Val
 1               5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (5)
<223> OTHER INFORMATION: modified residue = N-acylated amino acid

<400> SEQUENCE: 66

Arg Gln Arg Glu Leu
 1               5

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
```

```
<222> LOCATION: (1)
<223> OTHER INFORMATION: modified residue = N-acylated amino acid
<221> NAME/KEY: MOD_RES
<222> LOCATION: (5)
<223> OTHER INFORMATION: modified residue = N-acylated amino acid

<400> SEQUENCE: 67

Arg Gln Arg Glu Val
 1               5

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY:
<222> LOCATION: (1)
<223> OTHER INFORMATION: Xaa = any D-alpha amino acid
<221> NAME/KEY: MOD_RES
<222> LOCATION: (2)
<223> OTHER INFORMATION: modified residue = N-acylated amino acid
<221> NAME/KEY: MOD_RES
<222> LOCATION: (5)
<223> OTHER INFORMATION: modified residue = N-acylated amino acid

<400> SEQUENCE: 68

Xaa Arg Gln Arg Glu Ala
 1               5

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY:
<222> LOCATION: (1)
<223> OTHER INFORMATION: Xaa = any D-alpha amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (4)
<223> OTHER INFORMATION: modified residue = N-acylated amino acid

<400> SEQUENCE: 69

Xaa Leu Asp Arg Gln Arg
 1               5

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (4)
<223> OTHER INFORMATION: modified residue = N-methylated amino acid
<221> NAME/KEY: MOD_RES
<222> LOCATION: (5)
<223> OTHER INFORMATION: Xaa = any D-alpha amino acid, modified residue
      = N-acylated amino acid

<400> SEQUENCE: 70

Arg Asn Arg Glu Xaa Val
```

```
                  1               5
```

```
<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (4)
<223> OTHER INFORMATION: modified residue = N-acylated amino acid
<221> NAME/KEY:
<222> LOCATION: (6)
<223> OTHER INFORMATION: Xaa = any D-alpha amino acid

<400> SEQUENCE: 71

Arg Gln Arg Glu Val Xaa
  1               5

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (3)
<223> OTHER INFORMATION: modified residue = N-methylated amino acid
<221> NAME/KEY: MOD_RES
<222> LOCATION: (5)
<223> OTHER INFORMATION: Xaa = any D-alpha amino acid, modified residue
      = N-acylated amino acid

<400> SEQUENCE: 72

Arg Gln Arg Glu Xaa Val
  1               5

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (6)
<223> OTHER INFORMATION: modified residue = N-acylated amino acid

<400> SEQUENCE: 73

Arg Ala Pro Glu Arg Asn
  1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
```

```
<223> OTHER INFORMATION: modified residue = N-acylated amino acid
<221> NAME/KEY:
<222> LOCATION: (3)
<223> OTHER INFORMATION: Xaa = any D-alpha amino acid
<221> NAME/KEY: MOD_RES
<222> LOCATION: (4)
<223> OTHER INFORMATION: modified residue = N-acylated amino acid

<400> SEQUENCE: 74

Arg Gln Xaa Asp Val Arg
  1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (4)
<223> OTHER INFORMATION: modified residue = N-acylated amino acid
<221> NAME/KEY:
<222> LOCATION: (6)
<223> OTHER INFORMATION: Xaa = any D-alpha amino acid

<400> SEQUENCE: 75

Arg Gln Arg Asp Val Xaa
  1               5

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (3)
<223> OTHER INFORMATION: Xaa = any L-alpha amino acid
<221> NAME/KEY: MOD_RES
<222> LOCATION: (4)
<223> OTHER INFORMATION: modified residue = N-acylated amino acid

<400> SEQUENCE: 76

Arg Val Xaa Gln Arg Glu
  1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY:
<222> LOCATION: (3)
<223> OTHER INFORMATION: Xaa = any D-alpha amino acid
<221> NAME/KEY: MOD_RES
<222> LOCATION: (4)
<223> OTHER INFORMATION: modified residue = N-acylated amino acid

<400> SEQUENCE: 77
```

-continued

```
Gln Arg Xaa Glu Leu Arg
  1               5

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: Synthetic,
      modified residue = N-acylated amino acid
<221> NAME/KEY: MOD_RES
<222> LOCATION: (1)
<223> OTHER INFORMATION: modified residue = N-acylated amino acid
<221> NAME/KEY: MOD_RES
<222> LOCATION: (2)
<223> OTHER INFORMATION: modified residue = N-methylated amino acid
<221> NAME/KEY:
<222> LOCATION: (3)
<223> OTHER INFORMATION: Xaa = any D-alpha amino acid
<221> NAME/KEY: MOD_RES
<222> LOCATION: (4)
<223> OTHER INFORMATION: modified residue = N-acylated amino acid

<400> SEQUENCE: 78

Glu Gln Xaa Arg Leu Arg
  1               5
```